(12) United States Patent
Schraga

(10) Patent No.: US 9,044,552 B2
(45) Date of Patent: Jun. 2, 2015

(54) NEEDLE SAFETY SYSTEM AND METHOD

(75) Inventor: Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 349 days.

(21) Appl. No.: 12/755,921

(22) Filed: Apr. 7, 2010

(65) Prior Publication Data

US 2010/0286611 A1  Nov. 11, 2010

Related U.S. Application Data

(60) Provisional application No. 61/167,725, filed on Apr. 8, 2009.

(51) Int. Cl.
*A61M 5/00* (2006.01)
*A61M 5/32* (2006.01)
*A61M 5/158* (2006.01)

(52) U.S. Cl.
CPC ............. *A61M 5/3257* (2013.01); *A61M 5/158* (2013.01); *A61M 2005/3247* (2013.01); *A61M 2005/3249* (2013.01)

(58) Field of Classification Search
CPC .................. A61M 2005/3247; A61M 5/3243; A61M 25/0631; A61M 5/3202; A61M 5/3257; A61M 5/34; A61M 2005/3249; A61M 5/158
USPC ........................................................ 604/110
See application file for complete search history.

(56) References Cited

U.S. PATENT DOCUMENTS

| | | | |
|---|---|---|---|
| 4,650,468 A | 3/1987 | Jennings, Jr. | |
| 4,929,238 A | 5/1990 | Baum | |
| 5,002,533 A | 3/1991 | Jullien | |
| 5,057,087 A * | 10/1991 | Harmon | 604/198 |
| 5,098,402 A | 3/1992 | Davis | |
| 5,167,635 A | 12/1992 | Haber et al. | |
| 5,188,599 A | 2/1993 | Botich et al. | |
| 5,188,600 A | 2/1993 | Jullien | |
| 5,242,401 A | 9/1993 | Colsky | |
| 5,267,977 A | 12/1993 | Feeney, Jr. | |
| 5,308,329 A | 5/1994 | Mazur et al. | |
| 5,328,475 A | 7/1994 | Chen | |
| 5,336,198 A | 8/1994 | Silver et al. | |
| 5,344,403 A | 9/1994 | Lee | |
| 5,376,080 A | 12/1994 | Petrussa | |
| 5,403,286 A | 4/1995 | Lockwood, Jr. | |
| 5,498,241 A | 3/1996 | Fabozzi | |
| 5,569,203 A | 10/1996 | Chen | |
| 5,591,131 A | 1/1997 | Chen | |
| 5,591,138 A | 1/1997 | Vaillancourt | |

(Continued)

*Primary Examiner* — Jason Flick

(74) *Attorney, Agent, or Firm* — Greenblum & Bernstein, P.L.C.

(57) ABSTRACT

A needle device includes a body, a needle shield movable relative to the body, a needle at least partially arranged in the body, and a safety system that at least one of causes the needle shield to move to an extended position when activated by a user, releasably retains the needle shield in a retracted position after the user moves the needle shield to the retracted position, prevents a user from triggering the device, locks the needle shield in a fully extended position, prevents the needle shield from being retained in a retracted position after a user moves the needle shield towards the retracted position, non-releasably retains the needle shield in a fully extended position after being activated by a user, and utilizes two separate re-use prevent mechanisms. This Abstract is not intended to define the invention disclosed in the specification, nor intended to limit the scope of the invention in any way.

35 Claims, 22 Drawing Sheets

(56) References Cited

U.S. PATENT DOCUMENTS

| | | |
|---|---|---|
| 5,746,215 A | 5/1998 | Manjarrez |
| 5,814,017 A | 9/1998 | Kashmer et al. |
| 5,858,000 A | 1/1999 | Novacek et al. |
| 6,074,370 A | 6/2000 | Pressly, Sr. et al. |
| 6,074,373 A | 6/2000 | Sudo et al. |
| 6,090,078 A | 7/2000 | Erskine |
| 6,210,371 B1 | 4/2001 | Shaw |
| D452,000 S | 12/2001 | Crawford et al. |
| 6,375,640 B1 | 4/2002 | Teraoka |
| 6,461,328 B2 | 10/2002 | Wang et al. |
| 6,638,254 B2 | 10/2003 | Nakagami |
| 6,641,555 B1 | 11/2003 | Botich et al. |
| 6,648,849 B2 | 11/2003 | Tenhuisen et al. |
| 6,835,190 B2 | 12/2004 | Nguyen |
| 7,018,344 B2 | 3/2006 | Bressler et al. |
| 7,037,292 B2 | 5/2006 | Carlyon et al. |
| 7,097,633 B2 | 8/2006 | Botich et al. |
| 7,144,387 B2 | 12/2006 | Millerd |
| 7,150,725 B2 | 12/2006 | Wilkinson |
| 7,294,118 B2 | 11/2007 | Saulenas et al. |
| 7,322,963 B2 | 1/2008 | Goh |
| 7,413,560 B2 | 8/2008 | Chong et al. |
| 7,428,773 B2 | 9/2008 | Newby et al. |
| 2004/0254529 A1 | 12/2004 | Fitzgeald |
| 2006/0069347 A1* | 3/2006 | Besing .......................... 604/110 |
| 2006/0084913 A1 | 4/2006 | Lo |
| 2008/0015513 A1* | 1/2008 | Westbye et al. ............... 604/192 |
| 2008/0154212 A1 | 6/2008 | Schraga |
| 2008/0262421 A1 | 10/2008 | Schraga |
| 2008/0300549 A1* | 12/2008 | Verespej et al. ............... 604/198 |
| 2009/0069750 A1 | 3/2009 | Schraga |

* cited by examiner

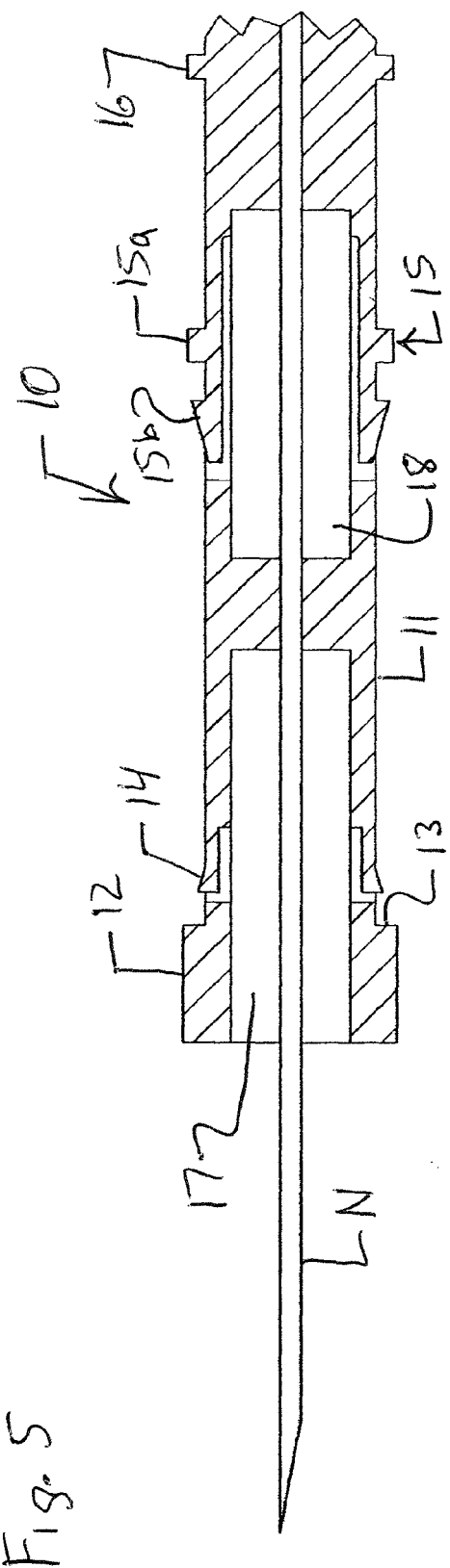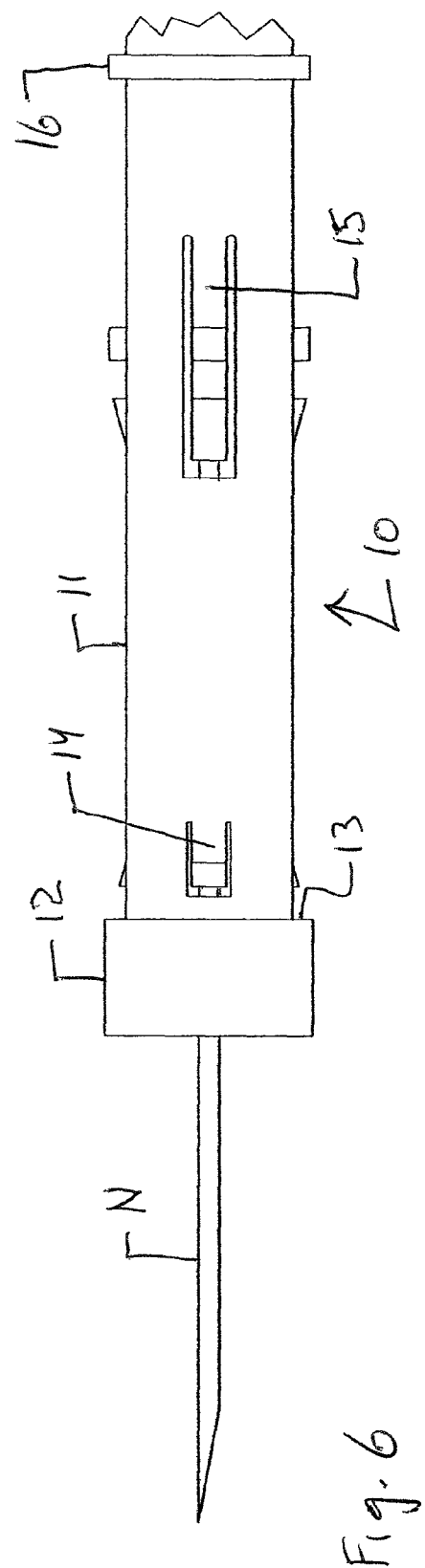
Fig. 5
Fig. 6

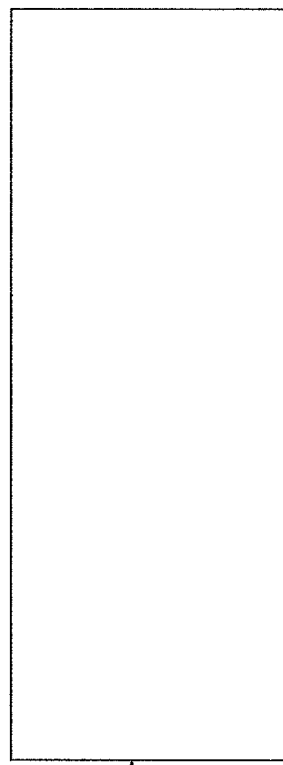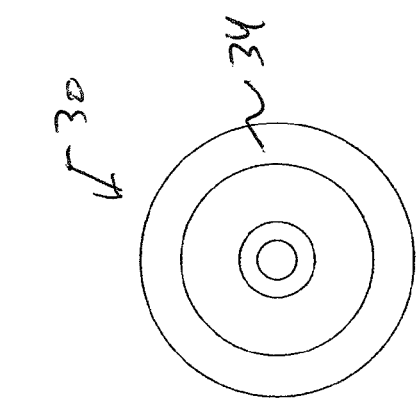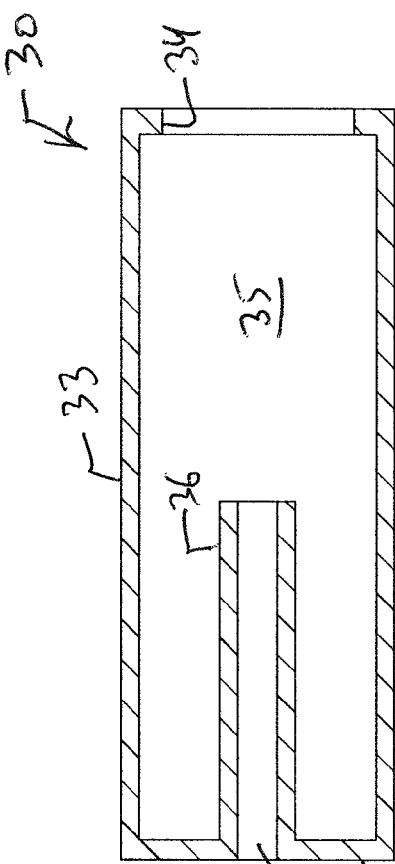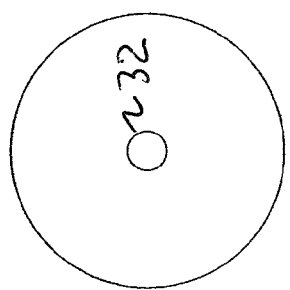

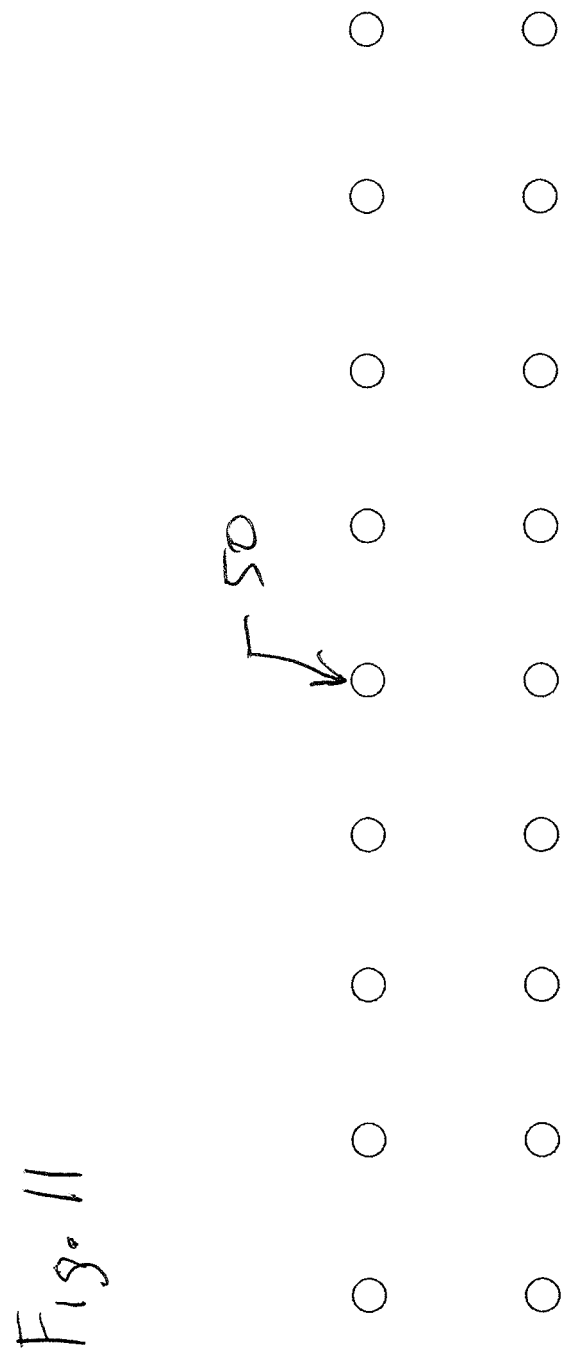

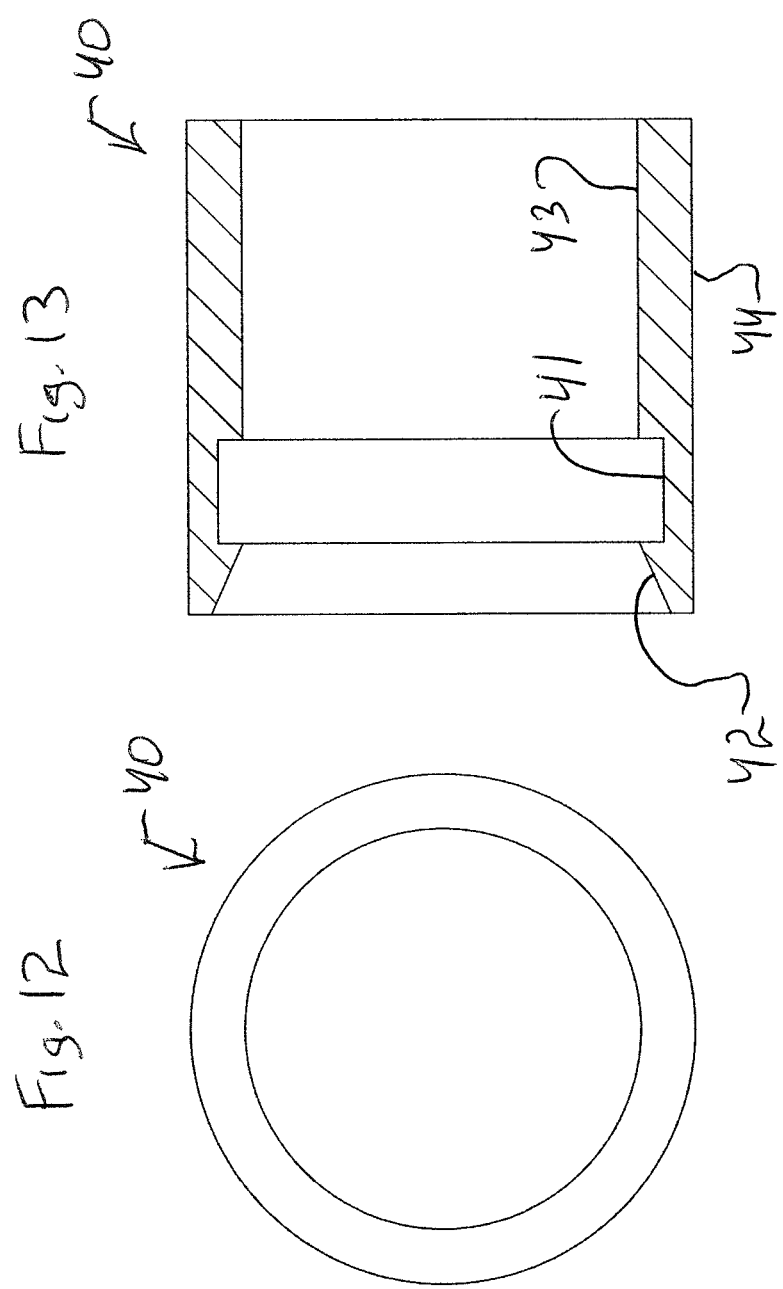

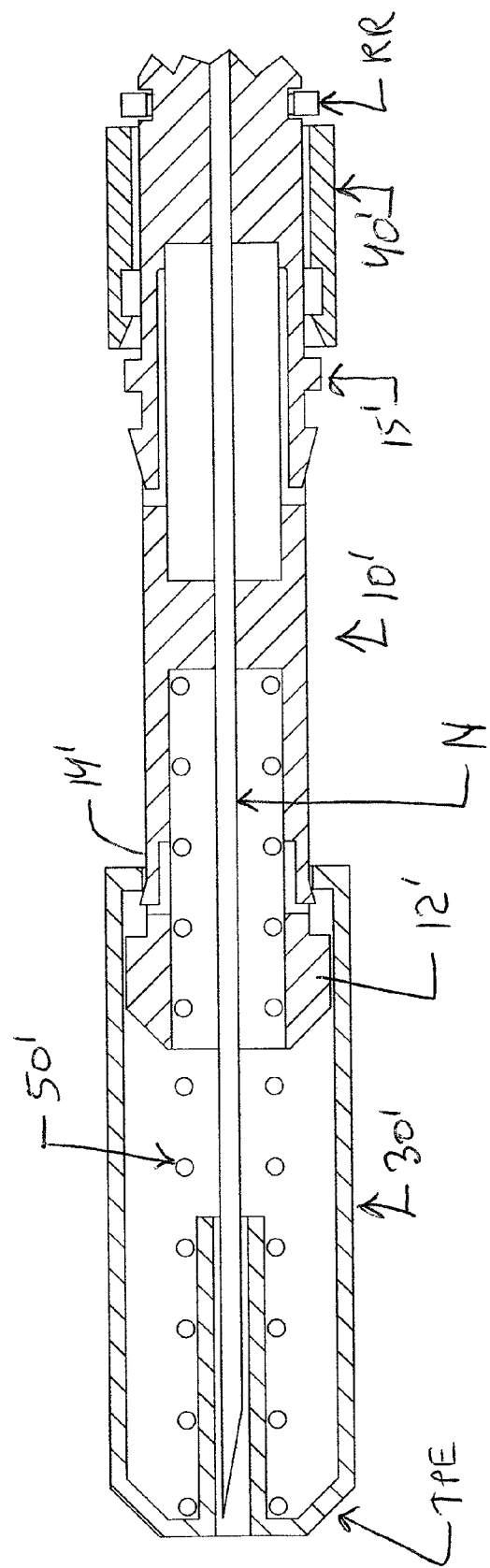

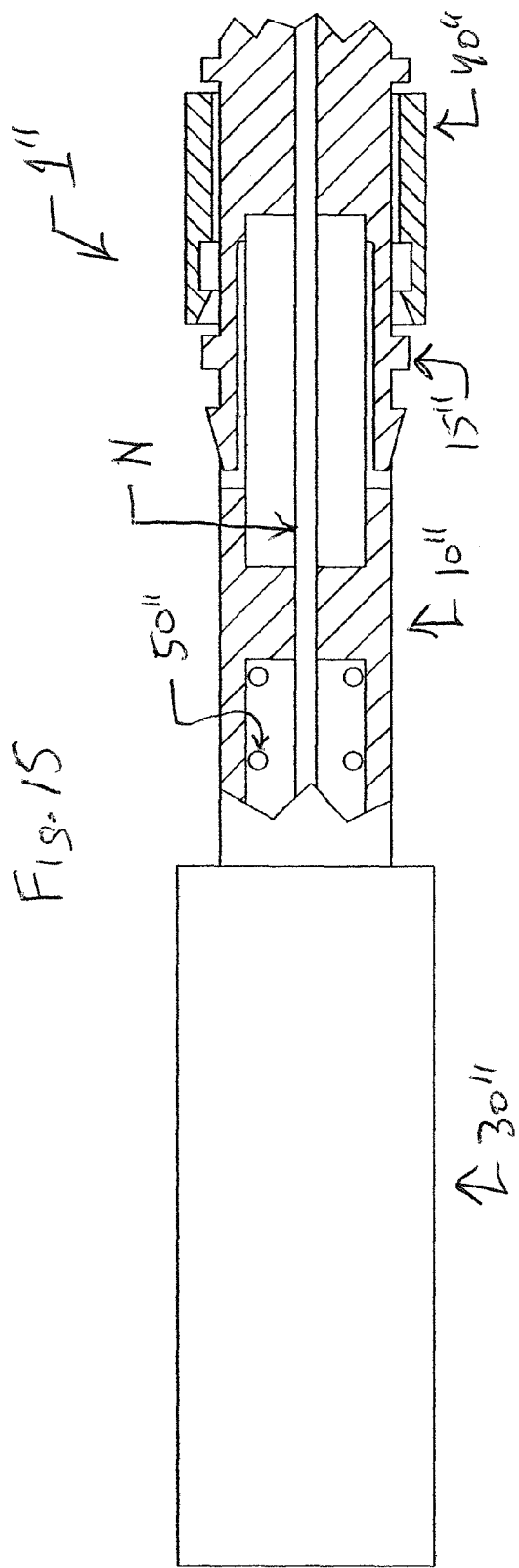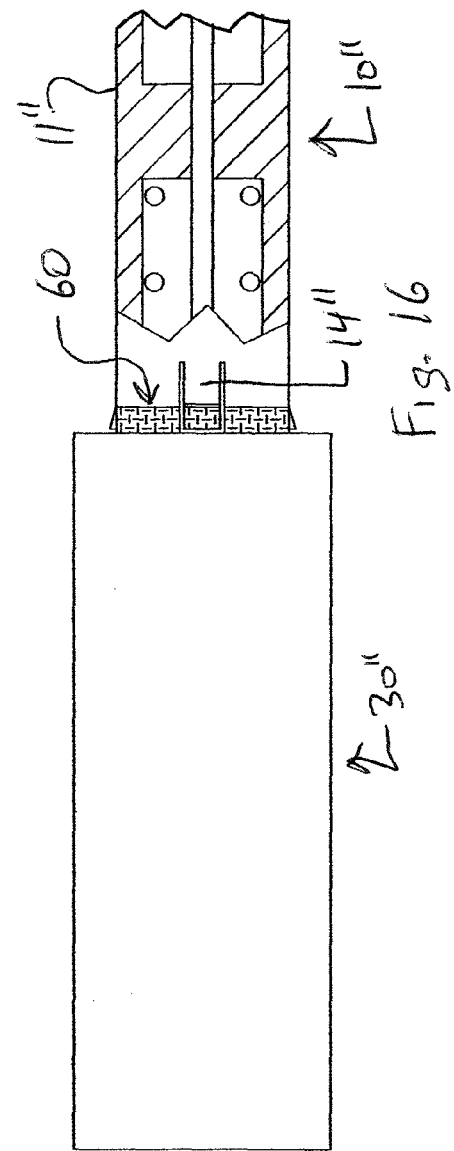

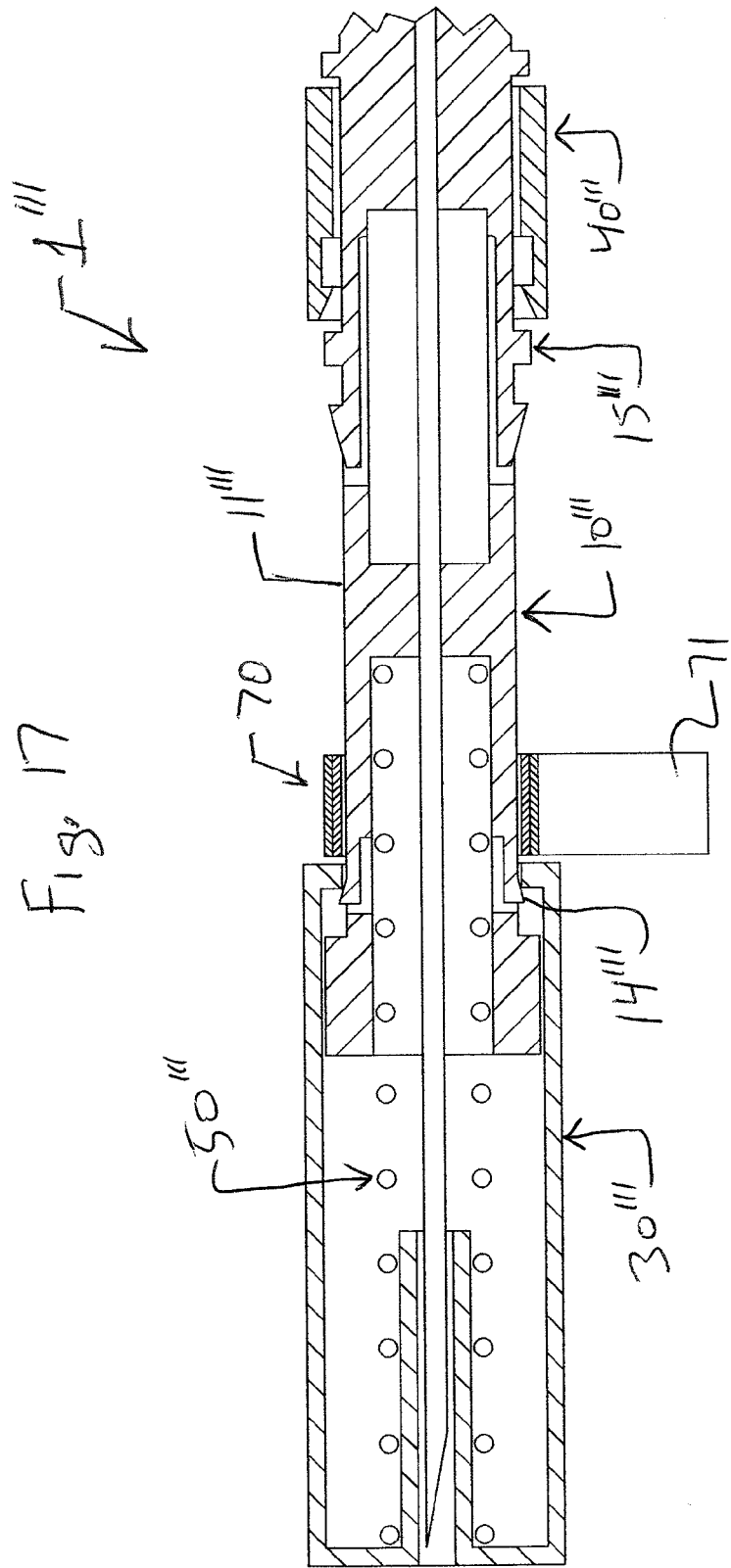

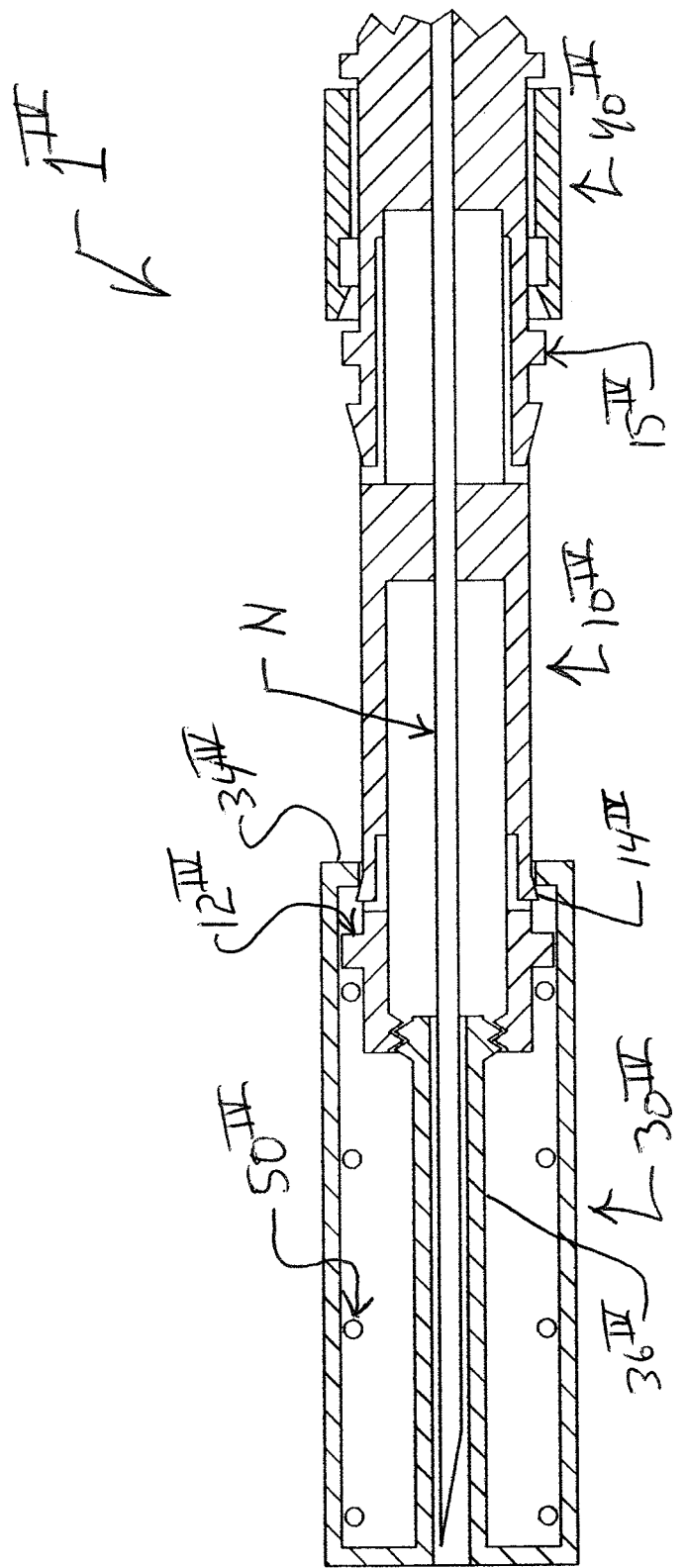

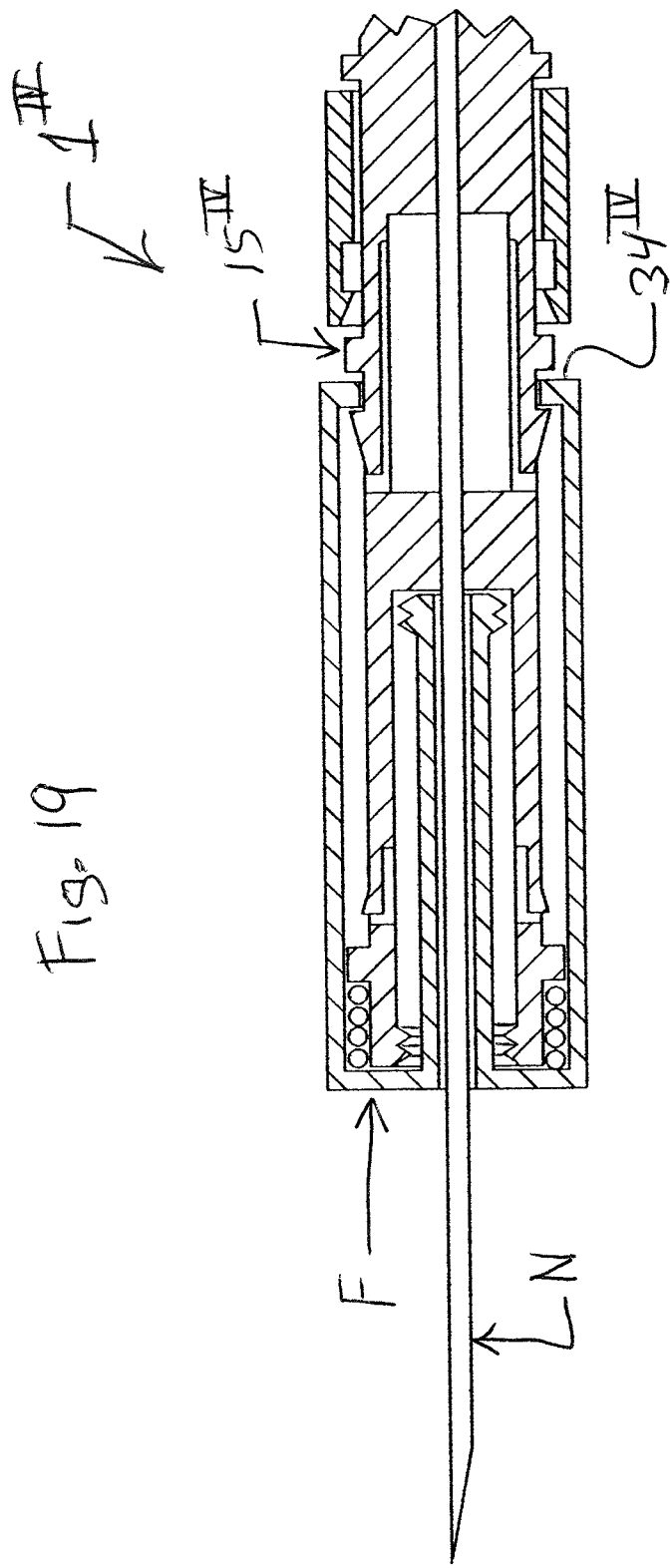

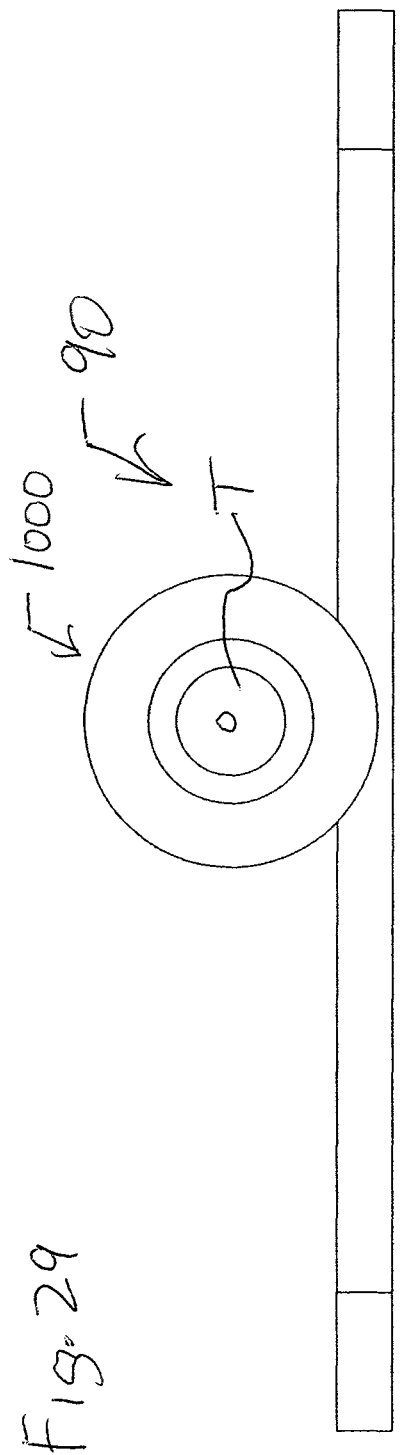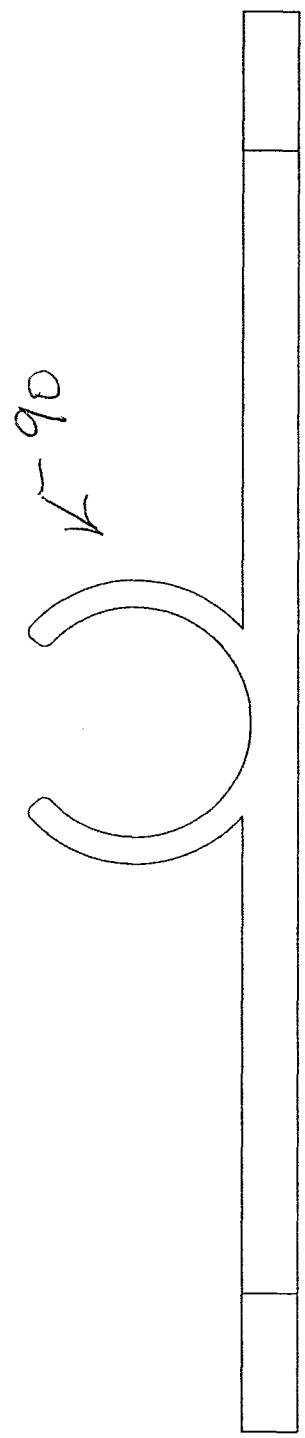

NEEDLE SAFETY SYSTEM AND METHOD

CROSS-REFERENCE TO RELATED APPLICATIONS

The instant application is a US non-provisional Application based on U.S. provisional application No. 61/167,725, filed Apr. 8, 2009, the disclosure of which is hereby expressly incorporated by reference hereto in its entirety.

BACKGROUND OF THE INVENTION

1. Field of the Invention

This invention relates generally to needle safety systems for injection devices, e.g., hypodermic syringes, IV infusion sets, etc., such as are utilized for injection of medicament into the body tissues of human and animal patients. More specifically, this invention relates to a needle safety system having a body, a safety shield, a needle, and a system for causing the safety shield to move from a retracted position to an extended position. The extended position preferably prevents the possibility of inadvertent needle pricks and/or prevents subsequent use or re-use of the system.

This invention also relates to single-use needle units which automatically deploy the safety shield over the needle when cause to do so and/or activated by the user.

This invention also relates to an IV infusion needle which can be used only once and have a built-in safety system which cannot be easily overridden by a user thereof.

2. Discussion of Background Information

The following devices relate to similar devices: U.S. Pat. No. 5,591,138 to VAILLANCOURT; U.S. Pat. No. 5,403,286 to LOCKWOOD, Jr.; U.S. Pat. No. 7,428,773 to NEWBY et al.; U.S. Pat. No. 7,413,560 to CHONG et al.; U.S. Pat. No. 7,322,963 to GOH; U.S. Pat. No. 7,150,725 to WILKINSON; U.S. Pat. No. 7,144,387 to MILLERD; U.S. Pat. No. 6,375,640 to TERAOKA; D452,000 to CRAWFORD et al; U.S. Pat. No. 5,498,241 to FABOZZI; U.S. Pat. No. 6,210,371 to SHAW; U.S. Pat. No. 5,376,080 to PETRUSSA; U.S. Pat. No. 5,267,977 to FEENEY, Jr.; U.S. Pat. No. 5,242,401 to COLSKY; and U.S. Pat. No. 5,167,635 to HABER et al. The entire disclosure of each of these documents is hereby expressly incorporated by reference in their entireties. The invention provides improvements over such devices such as using a more user friendly and/or less costly and/or more safe safety system.

SUMMARY OF THE INVENTION

According to one non-limiting aspect of the invention there is provided a needle device comprising a body, a needle shield movable relative to the body, a needle at least partially arranged in the body, and a safety system that at least one of causes the needle shield to move to an extended position when activated by a user, releasably retains the needle shield in a retracted position after the user moves the needle shield to the retracted position, prevents a user from triggering the device, locks the needle shield in a fully extended position, prevents the needle shield from being retained in a retracted position after a user moves the needle shield towards the retracted position, non-releasably retains the needle shield in a fully extended position after being activated by a user, and utilizes two separate re-use prevent mechanisms.

The device may be a single-use needle device. The body may be generally cylindrically shaped. The needle shield may be generally cylindrically shaped. The body may comprise a one-piece member. The needle shield may comprise a one-piece member. The body and the needle shield may each comprise a synthetic resin material. The needle may comprise a generally cylindrical hollow needle. The needle may comprise at least one of metal and stainless steel. The body may comprise at least one releasable retaining member which releasably retains the needle shield in a retracted position. The body may comprise plural releasable retaining members which releasably retains the needle shield in a retracted position. The body may comprise at least one non-releasable retaining member which non-releasably retains the needle shield in a fully extended position. The body may comprise at least one non-deflectable retaining member which non-releasably retains the needle shield in an extended position. The body may comprise plural non-releasable retaining members which lock the needle shield in an extended position.

The device may further comprise a trigger device that is structured and arranged to cause movement of the needle shield from the retracted position to the fully extended position.

The device may further comprise a trigger device that is structured and arranged to lock to the body after the device is triggered.

The needle shield may be movable from an initial position that is intermediate the fully extended position and the retracted position to the retracted position and then to the fully extended position. The needle shield may be movable to the retracted position from an initial position that is intermediate the fully extended position and the retracted position.

The device may further comprise a trigger that selectively releases at least one locking member which releasably retains the needle shield in the retracted position.

The device may further comprise a biasing member structured and arranged to move the needle shield from the retracted position to the fully extended position.

The device may further comprise a helical compression spring structured and arranged to move the needle shield from the retracted position to the fully extended position.

The device may further comprise a helical compression spring structured and arranged to maintain the needle shield in an initial position.

The safety system may cause the needle shield to move to the extended position when activated by a user. The safety system may releasably retain the needle shield in the retracted position after the user moves the needle shield to the retracted position. The safety system may prevent a user from triggering the device. The safety system may lock the needle shield in the fully extended position. The safety system may prevent the needle shield from being retained in the retracted position after a user moves the needle shield towards the retracted position. The safety system may non-releasably retain the needle shield in the fully extended position after being activated by a user. The safety system may utilize two separate re-use prevent mechanisms.

The device may further comprise a connecting interface for allowing the device to be mounted to an injection or sampling device. The connecting interface may have a Luer-Lok configuration.

The device may further comprise a system preventing the user from inadvertently moving the needle shield to the retracted position from an initial position. The system preventing the user from inadvertently moving the needle shield to the retracted position from the initial position may at least one of require the user to rotate unthread the needle shield from the body and require the user to remove a removable use prevention device.

The invention also provides for a single-use needle device comprising a body, a needle shield movable relative to the body, a needle at least partially arranged in the body, and a safety system that at least two of causes the needle shield to move to an extended position when activated by a user, releasably retains the needle shield in a retracted position after the user moves the needle shield to the retracted position, prevents a user from triggering the device, locks the needle shield in a fully extended position, prevents the needle shield from being retained in a retracted position after a user moves the needle shield towards the retracted position, non-releasably retains the needle shield in a fully extended position after being activated by a user, and utilizes two separate re-use prevent mechanisms.

The invention also provides for an IV infusion needle device comprising a body, a needle shield movable relative to the body, a needle at least partially arranged in the body, and a safety system that at least one of causes the needle shield to move to an extended position when activated by a user, releasably retains the needle shield in a retracted position after the user moves the needle shield to the retracted position, prevents a user from triggering the device, locks the needle shield in a fully extended position, prevents the needle shield from being retained in a retracted position after a user moves the needle shield towards the retracted position, non-releasably retains the needle shield in a fully extended position after being activated by a user, and utilizes two separate re-use prevent mechanisms.

The invention also provides for a method of using the device described above, wherein the method comprises moving the needle shield from an initial position to the retracted position, causing the needle shield to move to a fully extended position whereby the needle shield projects out beyond a needle tip, and at least one of preventing the needle shield from moving back to the initial position and preventing the needle shield from being retained in the retracted position.

The invention also provides for a needle device comprising at least one feature shown in at least one the drawings of the instant application.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows the device with the needle shield in an initial position and with the device being in a ready-to-use configuration;

FIG. 5 shows the device of FIG. 1 with the needle shield and trigger sleeve removed;

FIG. 6 shows the device of FIG. 5, but no longer in cross-section;

FIG. 7 shows a side view of the needle shield used in the embodiment of FIG. 1;

FIG. 8 shows a side cross-section view of the needle shield of FIG. 7;

FIG. 9 shows a front end view of the needle shield of FIG. 7;

FIG. 10 shows a rear end view of the needle shield of FIG. 7;

FIG. 11 shows a cross-section view of a needle shield biasing spring used the device of FIG. 1;

FIG. 12 shows a front end view of a trigger sleeve used the device of FIG. 1;

FIG. 13 shows a side cross-section view of a trigger sleeve used the device of FIG. 1;

FIG. 14 shows a side cross-section view of a second non-limiting embodiment of the device according to the invention. The needle portion is not shown in cross-section. The deflectable releasable locking member arranged behind the needle is not shown for clarity. FIG. 14 shows the device with the needle shield in an initial position and with the device being in a ready-to-use configuration. This embodiment is similar to the device of FIGS. 1-13 except that the needle shield and body has a tapered proximal end and the device utilizes a retaining ring to axially retain the trigger sleeve;

FIGS. 15 and 16 show partial side cross-section views of another non-limiting embodiment of the device. The deflectable members arranged behind the needle are not shown for purposes of clarity. This embodiment is similar to the device of FIGS. 1-13 except that the body utilizes a visual indicator to inform the user that the device has been used, i.e., that the needle shield has moved to the fully extended position and/or become non-releasably locked in this position and/or has already been used. FIG. 15 shows the device with the needle shield in an initial position. FIG. 16 shows the device after the needle shield has moved to a fully extended position and become non-releasably locked therein;

FIG. 17 shows a side cross-section view of another non-limiting embodiment of the device. The deflectable releasable locking member arranged behind the needle is not shown for clarity. This embodiment is similar to the device of FIGS. 1-13 except that it additionally utilizes a use prevention device or wrapping which must be removed by the user before the user can move the needle shield to the retracted position;

FIG. 18 shows a side cross-section view of another non-limiting embodiment of the device according to the invention. The needle portion is not shown in cross-section. The deflectable releasable locking member arranged behind the needle is not shown for clarity. FIG. 18 shows the device with the needle shield in an initial position and with the device being in a ready-to-use configuration. This embodiment is similar to the device of FIGS. 1-13 except that the needle shield threadably engages the body so as to prevention use of the device until the user rotates the needle shield. The threads also prevent the user from inadvertently moving the needle shield to the fully extended position;

FIG. 19 shows the device of FIG. 18 after the needle shield is unthreaded (unlocked) and moved by the user to the retracted position and is releasably retained therein;

FIG. 22 shows the device with the needle shield in an initial position. FIG. 23 shows the device after the needle shield has moved to a fully extended position and become non-releasably locked therein. The side cocked configuration of the needle shield shown in FIG. 23 provides an indication to the user that the device has already been used and prevents re-use because the opening is no longer aligned with the needle;

FIGS. 28-30 show various views of another non-limiting embodiment of the device. In FIG. 28, the deflectable releasable locking member arranged behind the needle is not shown for clarity. This embodiment is similar to the device of FIGS. 1-13 except that a rear or distal end of the device utilizes a connecting interface or configuration allowing the device to be connected to a tube of an IV infusion set and a distal area which can receive a butterfly member. FIG. 30 shows an end view of the butterfly member.

DETAILED DESCRIPTION OF THE INVENTION

Figure 1:
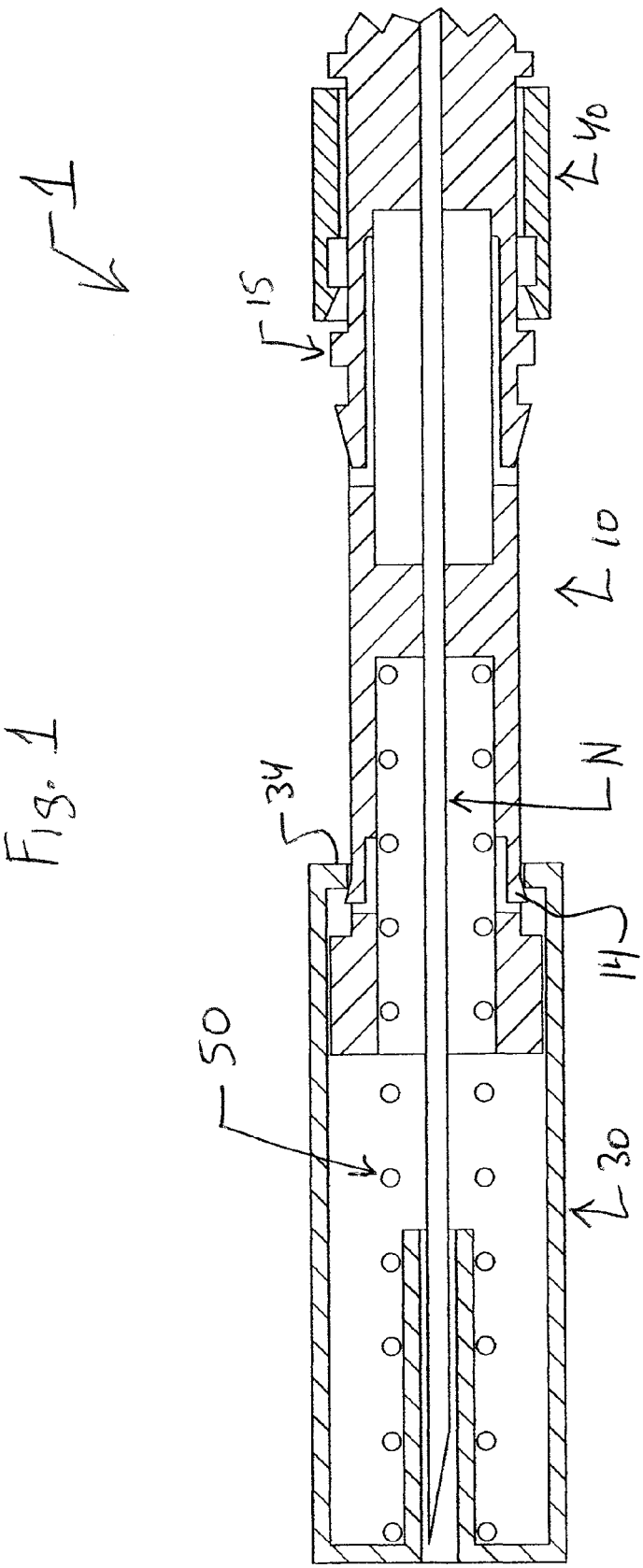
FIG. 1 shows a side cross-section view of a first non-limiting embodiment of the device according to the invention. The needle portion is not shown in cross-section. The deflectable retaining member and the deflectable releasable locking member arranged behind the needle is not shown for clarity.

Referring now to the drawings and first to FIGS. 1-13 which shows a first embodiment of an injection device 1. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. The device 1 includes an elongate generally cylindrical body or barrel 10 having a needle N retained therein. The needle N is hollow and has a proximal end that is configured for puncturing and a distal end for discharging or receiving fluid. The device 1 also utilizes an axially movable and retractable safety sleeve 30 arranged at a proximal end of the body 10 and an axially movable trigger sleeve 40 arranged at an area of a distal end of the body 10. Finally, the device 1 utilizes a spring 50 which is configured to bias the axially movable and retractable safety sleeve 30 towards an extended position covering the puncturing end of the needle N.

Referring to FIG. 1, the device 1 is shown in an initial or ready-to-use position. In this position, the needle shield 30 covers the proximal end of the needle N owing to the fact that the spring 50 biases the needle shield 30 towards the extended position. This position is maintained by contact between the distal flange 34 of the needle shield 30 and a plurality of deflectable projections 14. The position or configuration shown in FIG. 1 is, in embodiments, that which can be utilized when the device 1 is packaged.

Figure 2:
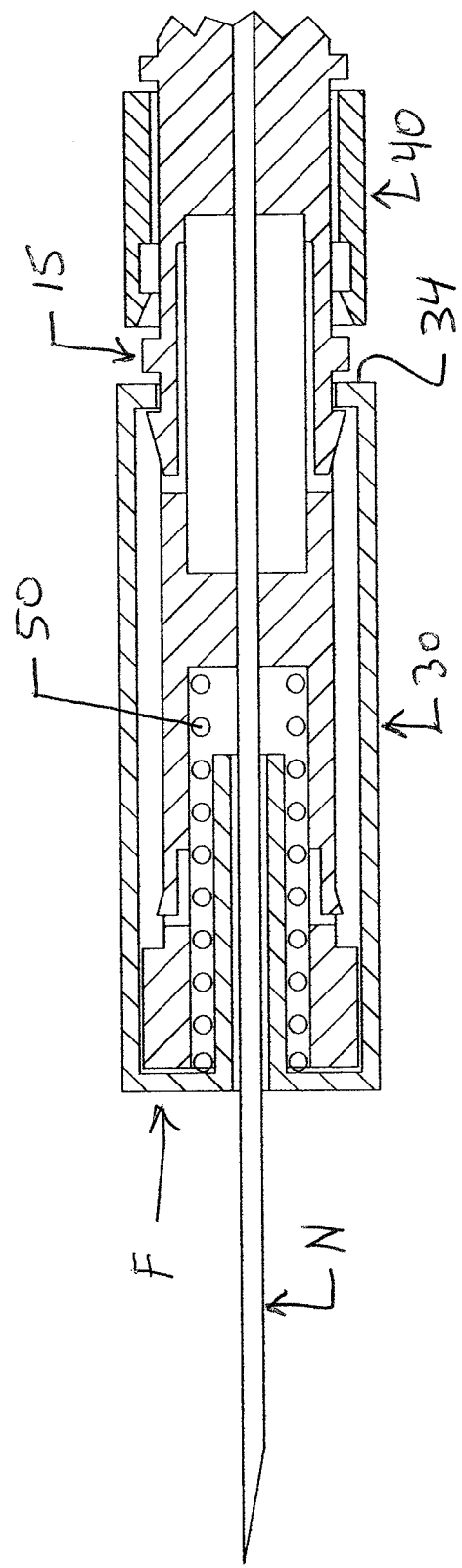
FIG. 2 shows the device of FIG. 1 with the needle shield being releasably locked in the retracted position after it is moved by the user to the retracted position.

Referring to FIG. 2, the device 1 is shown in a usable or using position. In this position, the needle shield 30 is retracted by the user (applying the equivalent of a force F sufficient to compress the spring 50) to expose the proximal end of the needle N. This occurs when the user moves the needle shield 30 back in a manner which compresses the spring 50. This retracted position is maintained by locking engagement between the distal flange 34 of the needle shield 30 and a plurality of deflectable locking members 15. The position or configuration shown in FIG. 2 is, in embodiments, that which can be utilized when the device 1, i.e., the puncturing end of the needle N, is injected.

Figure 3:
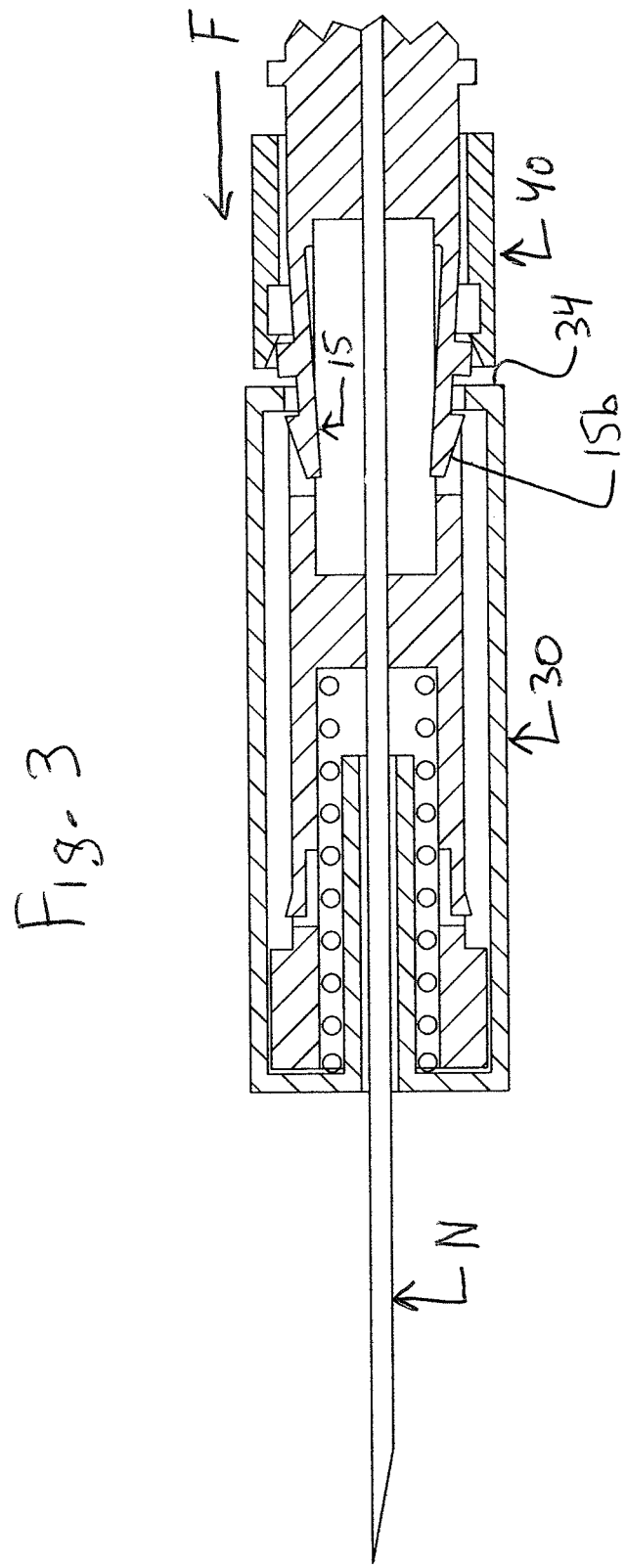
FIG. 3 shows the device of FIG. 2 in a triggered position after a trigger sleeve is moved to a triggering position that will allow the needle shield to move forwardly.

Referring to FIG. 3, the device 1 is shown in a post-use position. In this position, the needle shield 30 is ready to be released from the retracted by the user (applying the equivalent of a force F sufficient to move the trigger sleeve 40) and to move to a fully extended position (shown in FIG. 4) covering the proximal end of the needle N. This occurs when the user moves the trigger sleeve 40 forward in a manner which causes inward deflection of the locking members 15 (occurring also when the inside diameter of the flange 34 engages with tapered surfaces 15b) which in turn causes the members 15 to disengage and/or unlock from the flange 34. This triggering position in effect releases the locking engagement between the distal flange 34 of the needle shield 30 and a plurality of deflectable locking members 15. The position or configuration shown in FIG. 3 is, in embodiments, that which can be utilized immediately after the device 1 is used so that the device 1 will be rendered safe to handle and dispose.

Figure 4:
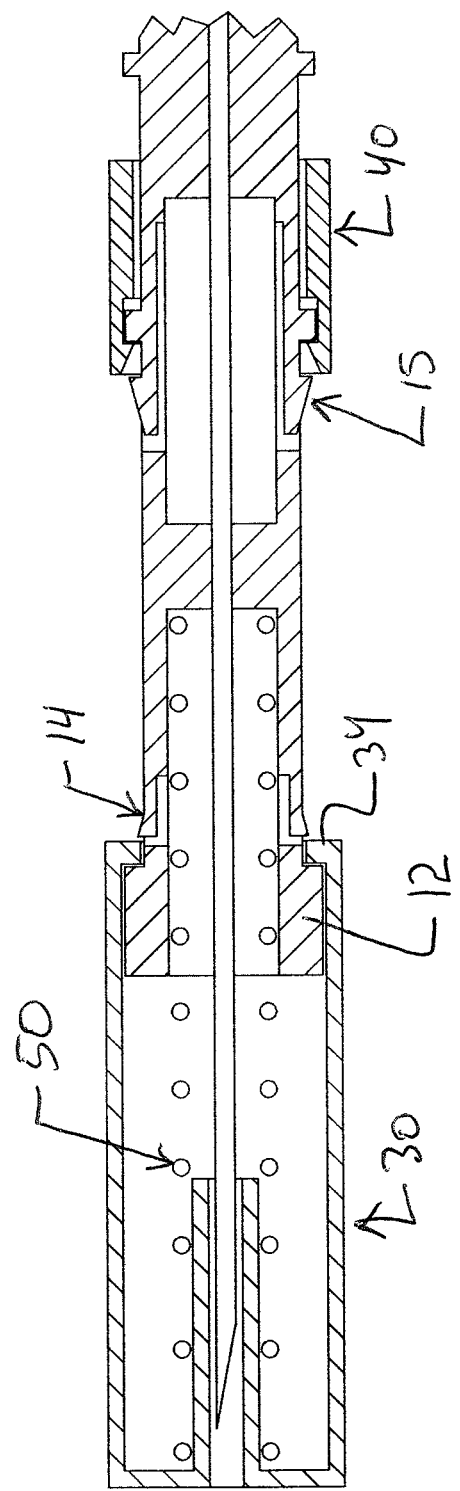
FIG. 4 shows the device of FIG. 3 after the needle shield has moved to a fully extended position and become non-releasably locked therein. The trigger sleeve is also non-releasably locked to the body. In this configuration, the device is rendered unusable and can be safely handled and discarded.

Referring to FIG. 4, the device 1 is shown in a final disposable position. In this position, the needle shield 30 has been automatically moved to the fully extended position by the spring 50 as soon as the device is triggered (see FIG. 3). As is apparent from a fair comparison of FIGS. 1 and 4, the spring 50 has caused the flange 34 to move forward of the deflectable members 14. The members 14 were thus to caused to deflect inwardly (as the flange 34 moved over them and slidably engaged with their tapered surfaces). The members 14 then spring back to an original position. The flange 34 thus cones to rest against a distal surface 13 (see FIGS. 5 and 6) of the shoulder 12 of the body 10. In this position, the needle shield 30 is non-removably locked in the fully extended position. This is due to the fact that the members 14 prevent substantial axial movement of the needle shield 30 relative to the body 10. This occurs because the members 14 each have an outer projecting portion that extends outwardly more than an inner diameter of the flange 34. In this position, the device 1 has been rendered single-use since the user no longer has the ability to retract the needle shield 30. Thus, locking the needle shield 30 in the fully extended position provides a first level of safety in preventing re-use of the device 1 and allows the user to handle the device 1 without fear of being pricked by the needle N. The device 1, however, also provides a second level of safety in regards to rendering the device single-use and/or providing an indication to the user that the device has already been used. This additional level of safety relates to the fact that the trigger sleeve 40 is non-releasably locked in the triggering position. This is due to the fact that the members 15 prevent substantial axial movement of the trigger sleeve 40 relative to the body 10. This occurs because the members 15 each have an outer projecting portion that extends into a groove 41 (see FIG. 13) outwardly more than an inner diameter 43 of the trigger sleeve 40. As is apparent from a fair comparison of FIGS. 1, 3 and 4, during triggering, the members 15 were caused to deflect inwardly (as the tapered surface 42 moves over the projections 15a of the members 15. The members 15 then spring back to an original position with the projections seated within the groove 41. The trigger sleeve 40 thus becomes non-releasably axially locked in the position shown in FIG. 4. The two safety systems described above are ensured because the user has no readily apparent mechanism to releasing the locking engagement between the body 10 and the needle shield 30 and between the body 10 and the trigger sleeve 40.

Referring to FIGS. 5 and 6, the body 10 is, in embodiments, a one-piece integrally formed member having a generally cylindrical main section 11, a generally cylindrical proximal section 12, an annular stop surface or shoulder 13 which is contacted by the flange 34 of the needle shield 30 in the fully extended position, four equally circumferentially spaced (i.e., arranged 90 degrees apart) deflectable retaining members 14 (for purposes of clarity the one behind the needle N in FIG. 5 is now shown), four equally circumferentially spaced (i.e., arranged 90 degrees apart) deflectable locking members 15 (for purposes of clarity the one behind the needle N in FIG. 5 is now shown), a retaining flange or shoulder 16 which limits axial movement of the trigger sleeve 40, a generally cylindrical proximal space 17 sized and configured to receive therein the spring 50 and to allow for inward deflection of the members 14, and an another generally cylindrical space 18 sized and configured to allow for inward deflection of the members 15. The members 14 have a tapered section which is contacted by the flange 34 of the needle shield 30 when in the position shown in FIG. 1 and can deflect inwardly and return or spring back to an original or relaxed position (see e.g., FIG. 5). The members 15 have a tapered section 15b which is contacted by the flange 34 of the needle shield 30 when moved to the retracted position shown in FIG. 2 and a projection 15a which is contacted by the tapered surface 42 of the trigger sleeve 40 (see FIGS. 3 and 13) when moved to the triggering position shown in FIG. 3, and can deflect inwardly (see e.g., FIG. 3) and return or spring back to an original or relaxed position (see e.g., FIG. 5). In embodiments, the device can utilize as few as two equally spaced members 14 and 15 and as many as ten of each.

Referring to FIGS. 7-10, the needle shield 30 is, in embodiments, a one-piece integrally formed member having an annular proximal end 31, a generally cylindrical main section 33, a generally cylindrical inner guide sleeve section 36, an annular stop flange 34, a generally cylindrical inner space 32 sized and configured to receive therein the needle N, and a generally cylindrical main space 35 sized and configured to receive therein the shoulder portion 12 of the body 10. In embodiments, the surface 33 can have a friction increasing portion, e.g., a knurl, a texture, etc., to make it easier to be gripped by a user.

Referring to FIG. 11, the spring 50 is, in embodiments, a one-piece integrally formed member having the form of a helical compression spring which, in embodiments, is made of spring steel.

Referring to FIGS. 12 and 13, the trigger sleeve 40 is, in embodiments, a one-piece integrally formed member having an annular proximal and distal ends, a tapered section 42, a generally cylindrical inner groove 41, a generally cylindrical inner surface 43 sized and configured to slidably engage with a comparably sized surface of the body 10, and a generally cylindrical main outer surface 44. In embodiments, the surface 44 can have a friction increasing portion, e.g., a knurl, a texture, etc., to make it easier to be gripped by a user.

Referring now to FIG. 14 which shows another embodiment of an injection device 1'. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device 1' includes an elongate generally cylindrical body or barrel 10' having a needle N retained therein. The needle N is hollow and has a proximal end that is configured for puncturing and a distal end for discharging or receiving fluid. The device 1' also utilizes an axially movable and retractable safety sleeve 30' arranged at a proximal end of the body 10' and an axially movable trigger sleeve 40' arranged at an area of a distal end of the body 10'. Finally, the device 1' utilizes a spring 50' which is configured to bias the axially movable and retractable safety sleeve 30' towards an extended position covering the puncturing end of the needle N. The deflectable member 14' and 15' arranged behind the needle N are not shown for clarity. This embodiment is similar to the device of FIGS. 1-13 except that the needle shield 30' and body 10' have comparable tapered proximal ends TPE and the device 1' optionally utilizes a separate retaining ring RR to axially retain the trigger sleeve 40'.

Referring now to FIGS. 15 and 16, which show another embodiment of an injection device 1". In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the first embodiment, the device 1" includes an elongate generally cylindrical body or barrel 10" having a needle N retained therein. The needle N is hollow and has a proximal end that is configured for puncturing and a distal end for discharging or receiving fluid. The device 1" also utilizes an axially movable and retractable safety sleeve 30" arranged at a proximal end of the body 10" and an axially movable trigger sleeve 40" arranged at an area of a distal end of the body 10". Finally, the device 1" utilizes a spring 50" which is configured to bias the axially movable and retractable safety sleeve 30" towards an extended position covering the puncturing end of the needle N. The deflectable member 14" and 15" arranged behind the needle N are not shown for clarity. This embodiment is similar to the device of FIGS. 1-13 except that the body 10" utilizes a visual indicator 60 to inform the user that the device 1" has been used, i.e., that the needle shield 30" has moved to the fully extended position and/or become non-releasably locked in this position and/or has already been used. FIG. 15 shows the device 1" with the needle shield in an initial position (similar to FIG. 1). FIG. 16 shows the device 1" after the needle shield 30" has moved to a fully extended position and become non-releasably locked therein. In the fully extended position, the visual indicator 60 is now visible whereas it was previously covered by a distal portion of the needle shield 30" in FIG. 15. In embodiments, the visual indicator 60 is a colored band, i.e., a narrow section of having a color that is different from that of the surface 11". Other forms of visual indication can also be utilized which are not visible in the configuration of FIG. 15, but are visible in the configuration of FIG. 16.

Referring now to FIG. 17, which show another embodiment of an injection device 1'''. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the first embodiment, the device 1''' includes an elongate generally cylindrical body or barrel 10''' having a needle N retained therein. The needle N is hollow and has a proximal end that is configured for puncturing and a distal end for discharging or receiving fluid. The device 1''' also utilizes an axially movable and retractable safety sleeve 30''' arranged at a proximal end of the body 10''' and an axially movable trigger sleeve 40''' arranged at an area of a distal end of the body 10'''. Finally, the device 1''' utilizes a spring 50''' which is configured to bias the axially movable and retractable safety sleeve 30''' towards an extended position covering the puncturing end of the needle N. The deflectable member 14''' and 15''' arranged behind the needle N are not shown for clarity. This embodiment is similar to the device of FIGS. 1-13 except that it additionally utilizes a removable retaining member 70 arranged on the body 10'''. The member 70 serves to inform the user that the device 1''' has not yet been used and also prevents accidental rearward movement of the needle shield 30'''. In order to use the device 1''', the user first removes the member 70 and then uses the device in the same way as described above regarding the embodiment of FIGS. 1-13. FIG. 17 shows the device 1''' with the needle shield in an initial position (similar to FIG. 1). In embodiments, the member 70 is a colored adhesive wrap, i.e., a narrow section of adhesive tape having a color that is different from that of the surface 11'''. Other forms of the member 70 can also be utilized which prevent rearward axial movement of the needle shield 30''' until removed. The member 70 has a protruding free end 71 which can be gripped by the user to allow for unwrapping from the surface 11'''.

Referring now to FIGS. 18-21, which show another embodiment of an injection device $1^{IV}$. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the first embodiment, the device $1^{IV}$ includes an elongate generally cylindrical body or barrel $10^{IV}$ having a needle N retained therein. The needle N is hollow and has a proximal end that is configured for puncturing and a distal end for discharging or receiving fluid. The device $1^{IV}$ also utilizes an axially movable and retractable safety sleeve $30^{IV}$ arranged at a proximal end of the body $10^{IV}$ and an axially movable trigger sleeve $40^{IV}$ arranged at an area of a distal end of the body $10^{IV}$. Finally, the device $1^{IV}$ utilizes a spring $50^{IV}$ which is configured to bias the axially movable and retractable safety sleeve $30^{IV}$ towards an extended position covering the puncturing end of the needle N. The deflectable member $14^{IV}$ and $15^{IV}$ arranged behind the needle N are not shown for clarity.

Referring to FIG. 18, the device $1^{IV}$ is shown in an initial or ready-to-use position. In this position, the needle shield $30^{IV}$ covers the proximal end of the needle N owing to the fact that the spring $50^{IV}$ biases the needle shield $30^{IV}$ towards the extended position and because external thread of section $36^{IV}$ threadably engage with internal threads arranged on a proximal end of the body $10^{IV}$. This position is thus maintained by both contact between the distal flange $34^{IV}$ of the needle shield $30^{IV}$ and a plurality of deflectable projections $14^{IV}$, but mainly as a result of the engagement between external thread of section $36^{IV}$ and internal threads arranged on a proximal end of the body $10^{IV}$. The position or configuration shown in FIG. 18 is, in embodiments, that which can be utilized when the device $1^{IV}$ is packaged and ensures that the needle shield $30^{IV}$ cannot substantially move axially forwards or backwards relative to the body $10^{IV}$.

Referring to FIG. 19, the device $1^{IV}$ is shown in a usable or using position. In this position, the needle shield $30^{IV}$ is retracted by the user (applying the equivalent of a force F sufficient to compress the spring $50^{IV}$) to expose the proximal end of the needle N. This occurs when the user moves the needle shield $30^{IV}$ back in a manner which compresses the spring $50^{IV}$. This retracted position is maintained by locking engagement between the distal flange $34^{IV}$ of the needle shield $30^{IV}$ and a plurality of deflectable locking members $15^{IV}$. The position or configuration shown in FIG. 19 is, in embodiments, that which can be utilized when the device $1^{IV}$, i.e., the puncturing end of the needle N, is injected. In order to cause rearward movement of the needle shield $30^{IV}$, the user first rotates the needle shield $30^{IV}$ relative to the body $10^{IV}$ in a first rotation direction which causes the threaded engagement between the needle shield $30^{IV}$ and the body $10^{IV}$ to disengage. Then, the user causes rearward movement of the needle shield $30^{IV}$ as in the embodiment shown in FIG. 2.

Figure 20:
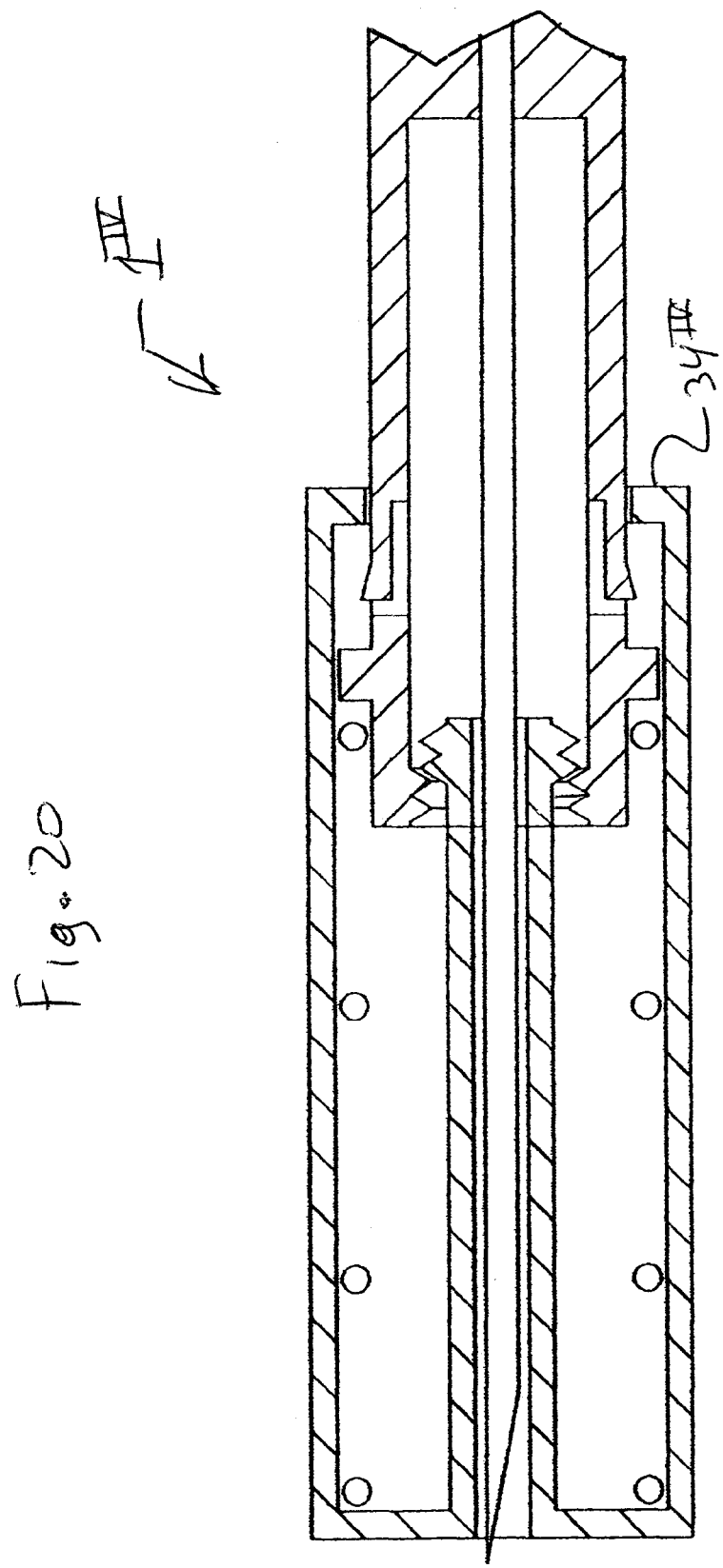
FIG. 20 shows the device of FIG. 19 after the needle shield has moved to an intermediate position just prior to the fully extended position wherein it will become non-releasably locked therein. Although not shown, in this position the trigger sleeve is also non-releasably locked to the body.

Referring to FIG. 20, the device $1^{IV}$ is shown in a post-use and triggered position. In this position, the needle shield $30^{IV}$ has been released from the retracted by the user (applying the equivalent of a force F sufficient to move the trigger sleeve $40^{IV}$) and to move to an intermediate position just short of the fully extended position (shown in FIG. 21) covering the proximal end of the needle N. This occurs when the user moves the trigger sleeve $40^{IV}$ forward in a manner which causes inward deflection of the locking members $15^{IV}$ which in turn causes the members $15^{IV}$ to disengage and/or unlock from the flange 34. This triggering position in effect releases the locking engagement between the distal flange $34^{IV}$ of the needle shield $30^{IV}$ and a plurality of deflectable locking members $15^{IV}$. The position or configuration shown in FIG. 20 is, in embodiments, that which can be utilized immediately after the device $1^{IV}$ is used so that the device $1^{IV}$ will be rendered somewhat safer to handle.

Figure 21:
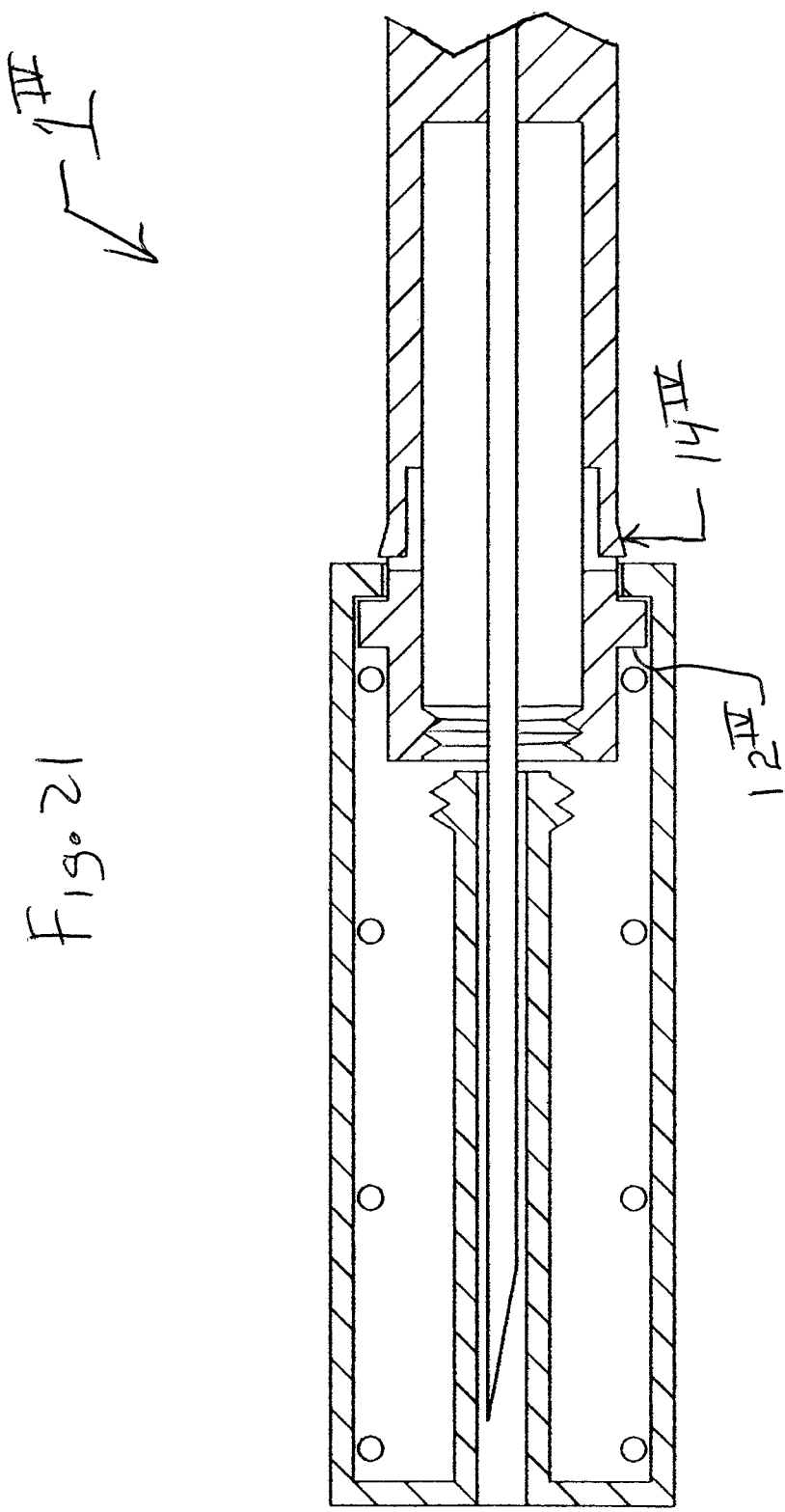
FIG. 21 shows the device of FIG. 20 after the needle shield has been threaded towards the forward end and moved to a fully extended position by the user rotating the needle shield in a direction opposite that use to allow the user to move it to the retracted position. The needle shield has become non-releasably locked therein.

Referring to FIG. 21, the device $1^{IV}$ is shown in a final disposable position. In this position, the needle shield $30^{IV}$, which was automatically moved to the position shown in FIG. 20 by the spring $50^{IV}$, is moved to the fully extended position first by the user rotating the needle shield $30^{IV}$ relative to the body $10^{IV}$ in a second opposite direction to cause engagement of the threads. Once the threads disengage with one another, the spring $50^{IV}$ will automatically cause the needle shield $30^{IV}$ to move to the fully extended position shown in FIG. 21. As is apparent from a fair comparison of FIGS. 18 and 21, the spring $50^{IV}$ has caused the flange $34^{IV}$ to move forward of the deflectable members $14^{IV}$. The members $14^{IV}$ were thus to caused to deflect inwardly (as the flange $34^{IV}$ moved over them and slidably engaged with their tapered surfaces). The members $14^{IV}$ then spring back to an original position. The flange $34^{IV}$ thus cones to rest against a distal surface of the shoulder $12^{IV}$ of the body $10^{IV}$. In this position, the needle shield $30^{IV}$ is non-removably locked in the fully extended position. This is due to the fact that the members $14^{IV}$ prevent substantial axial movement of the needle shield $30^{IV}$ relative to the body $10^{IV}$. This occurs because the members $14^{IV}$ each have an outer projecting portion that extends outwardly more than an inner diameter of the flange $34^{IV}$. In this position, the device $1^{IV}$ has been rendered single-use since the user no longer has the ability to retract the needle shield $30^{IV}$. Should this locking engagement fail, the user will still be prevented from moving the needle shield $30^{IV}$ to the retracted position by the threads (unless the user deliberately rotates the needle shield $30^{IV}$ in a manner which causes engagement between the threads. Thus, locking the needle shield $30^{IV}$ in the fully extended position provides a first level of safety in preventing re-use of the device $1^{IV}$ and allows the user to handle the device $1^{IV}$ without fear of being pricked by the needle N. The device $1^{IV}$, however, also provides a second level of safety in regards to rendering the device single-use and/or providing an indication to the user that the device has already been used. This additional level of safety relates to the fact that the trigger sleeve $40^{IV}$ is non-releasably locked in the triggering position in a manner similar to that described above regarding FIG. 4. The two, or more accurately three, safety systems described above are ensured because the user has no readily apparent mechanism to releasing the locking engagement between the body $10^{IV}$ and the needle shield $30^{IV}$ and between the body $10^{IV}$ and the trigger sleeve $40^{IV}$.

Figure 22:
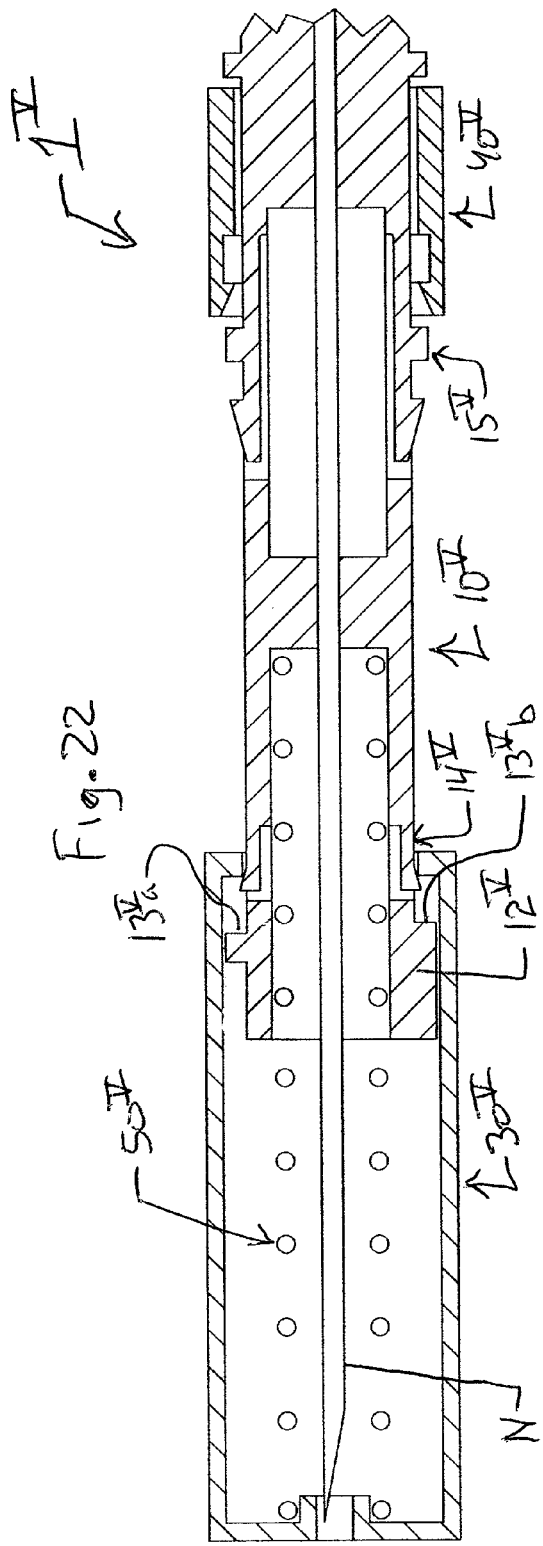
FIGS. 22 and 23 show side cross-section views of another non-limiting embodiment of the device. The deflectable releasable locking member arranged behind the needle is not shown for clarity. This embodiment is similar to the device of FIGS. 1-13 except that the needle shield has a very short needle guide and the body is configured to cause a side cocking of the needle shield when it moved to the fully extended position.
Figure 23:
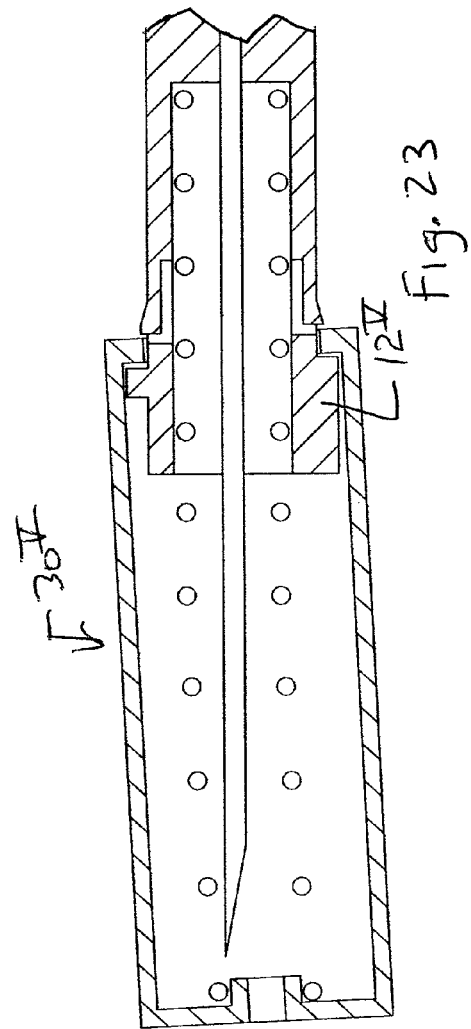

Referring now to FIGS. 22 and 23, which show another embodiment of an injection device $1^V$. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the first embodiment, the device $1^V$ includes an elongate generally cylindrical body or barrel $10^V$ having a needle N retained therein. The needle N is hollow and has a proximal end that is configured for puncturing and a distal end for discharging or receiving fluid. The device $1^V$ also utilizes an axially movable and retractable safety sleeve $30^V$ arranged at a proximal end of the body $10^V$ and an axially movable trigger sleeve $40^V$ arranged at an area of a distal end of the body $10^V$. Finally, the device $1^V$ utilizes a spring $50^V$ which is configured to bias the axially movable and retractable safety sleeve $30^V$ towards an extended position covering the puncturing end of the needle N. The deflectable member $14^V$ and $15^V$ arranged behind the needle N are not shown for clarity. This embodiment is similar to the device of FIGS. 1-13 except that the body $10^V$ utilizes a proximal shoulder $12^V$ which has upper and lower stop surfaces that result in the needle shield $30^V$ assuming a side cocked position (because of the different axial locations of stop surfaces $13^V a$ and $13^V b$) when it moves to the fully extended position (see FIG. 23). This provides an indication to the user that the device has already been used. It also prevents the user from moving the needle shield $30^V$ back to a retracted position. FIG. 22 shows the device $1^V$ with the needle shield $30^V$ in an initial position (similar to FIG. 1). FIG. 23 shows the device $1^V$ after the needle shield $30^V$ has moved to a fully extended position and become cocked and non-releasably locked therein. In the fully extended position, the visual indication is provided by the cocked configuration of the needle shield $30^V$.

Figure 24:
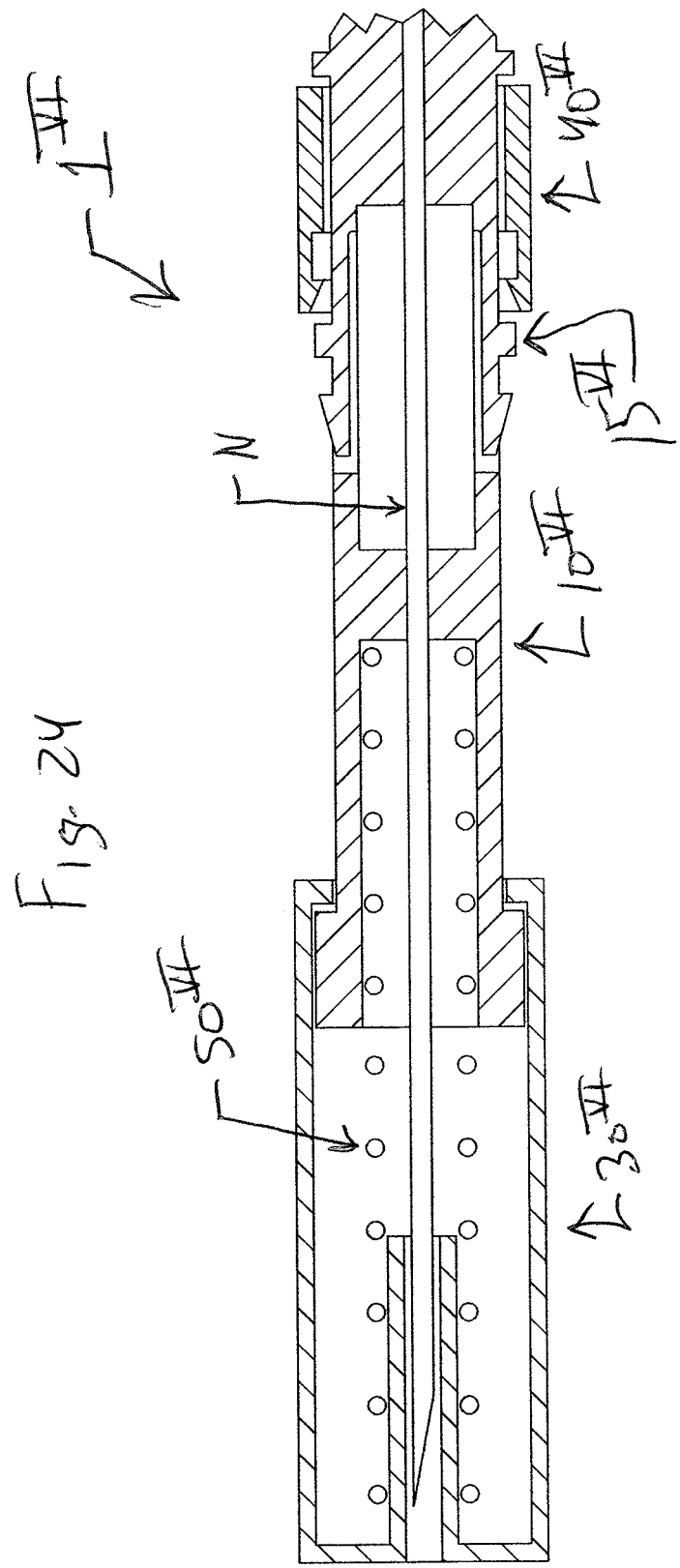
FIG. 24 shows a side cross-section view of another non-limiting embodiment of the device. The deflectable releasable locking member arranged behind the needle is not shown for clarity. This embodiment is similar to the device of FIGS. 1-13 except that the initial position of the needle shield is the same as the fully retracted position and the device lacks mechanism for non-releasably locking the needle shield in the extended position.

Referring now to FIG. 24 which shows another embodiment of an injection device $1^{VI}$. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device $1^{VI}$ includes an elongate generally cylindrical body or barrel $10^{VI}$ having a needle N retained therein. The needle N is hollow and has a proximal end that is configured for puncturing and a distal end for discharging or receiving fluid. The device $1^{VI}$ also utilizes an axially movable and retractable safety sleeve $30^{VI}$ arranged at a proximal end of the body $10^{VI}$ and an axially movable trigger sleeve $40^{VI}$ arranged at an area of a distal end of the body $10^{VI}$. Finally, the device $1^{VI}$ utilizes a spring $50^{VI}$ which is configured to bias the axially movable and retractable safety sleeve $30^{VI}$ towards an extended position covering the puncturing end of the needle N. Unlike the previous embodiments, however, this embodiment utilizes no deflectable members to retain the needle shield $30^{VI}$ in the fully extended position, and, in fact, the original position of the needle shield is the same as the final extended position. The deflectable member $15^{VI}$ arranged behind the needle N is not shown for clarity. This embodiment is otherwise similar to the device of FIGS. 1-13.

Figure 25:
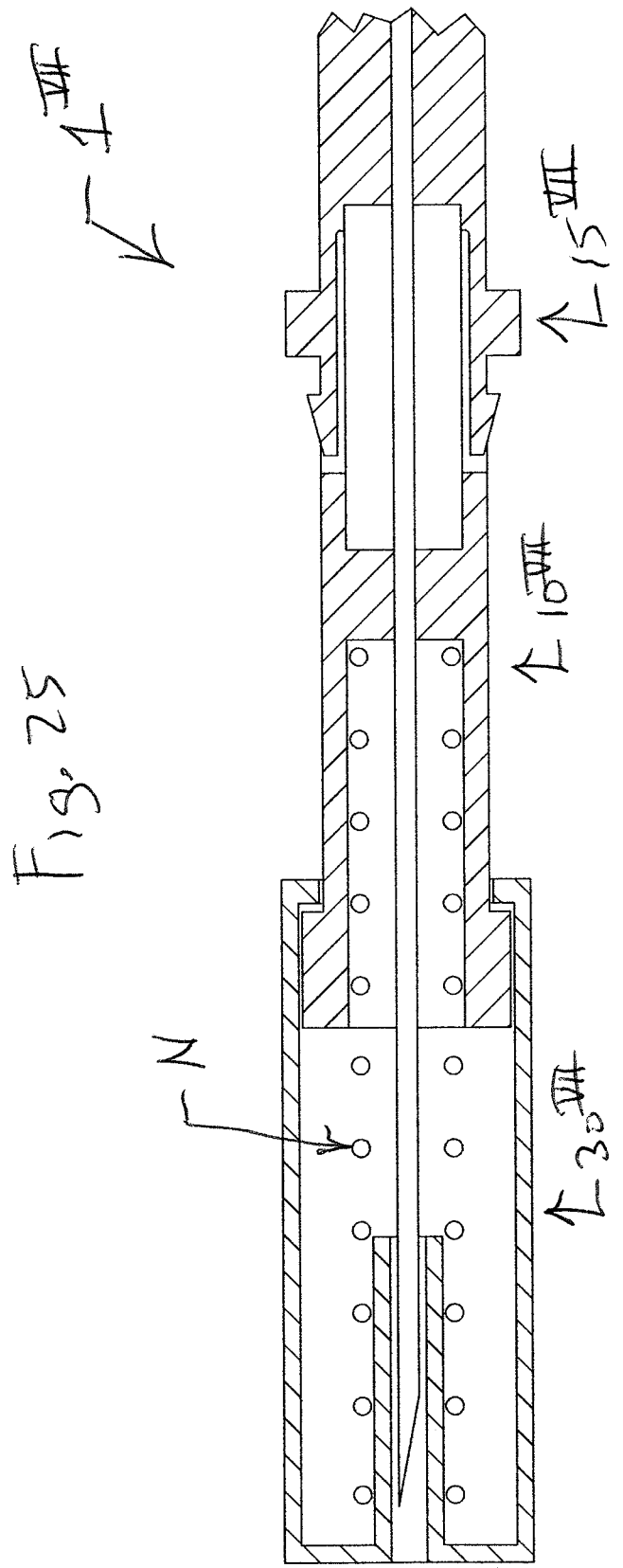
FIG. 25 shows a side cross-section view of another non-limiting embodiment of the device. This embodiment is similar to the device of FIG. 24 except that the trigger sleeve is removed so that the device can be triggered by the user depressing the releasably locking devices.

Referring now to FIG. 25 which shows another embodiment of an injection device $1^{VII}$. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device $1^{VII}$ includes an elongate generally cylindrical body or barrel $10^{VII}$ having a needle N retained therein. The needle N is hollow and has a proximal end that is configured for puncturing and a distal end for discharging or receiving fluid. The device $1^{VII}$ also utilizes an axially movable and retractable safety sleeve $30^{VII}$ arranged at a proximal end of the body $10^{VII}$. Finally, the device $1^{VII}$ utilizes a spring $50^{VII}$ which is configured to bias the axially movable and retractable safety sleeve $30^{VII}$ towards an extended position covering the puncturing end of the needle N. Unlike the previous embodiments, however, this embodiment utilizes no deflectable members to retain the needle shield $30^{VII}$ in the fully extended position, and, in fact, the original position of the needle shield is the same as the final extended position. Also, unlike the previous embodiments, this embodiment utilizes no an axially movable trigger sleeve. Instead, the user directly depresses the deflectable members $15^{VII}$ to cause the needle shield $30^{VII}$ to move to the fully extended position from the retracted position. The deflectable member $15^{VII}$ arranged behind the needle N is not shown for clarity. This embodiment is otherwise similar to the device of FIG. 24.

Figure 26:
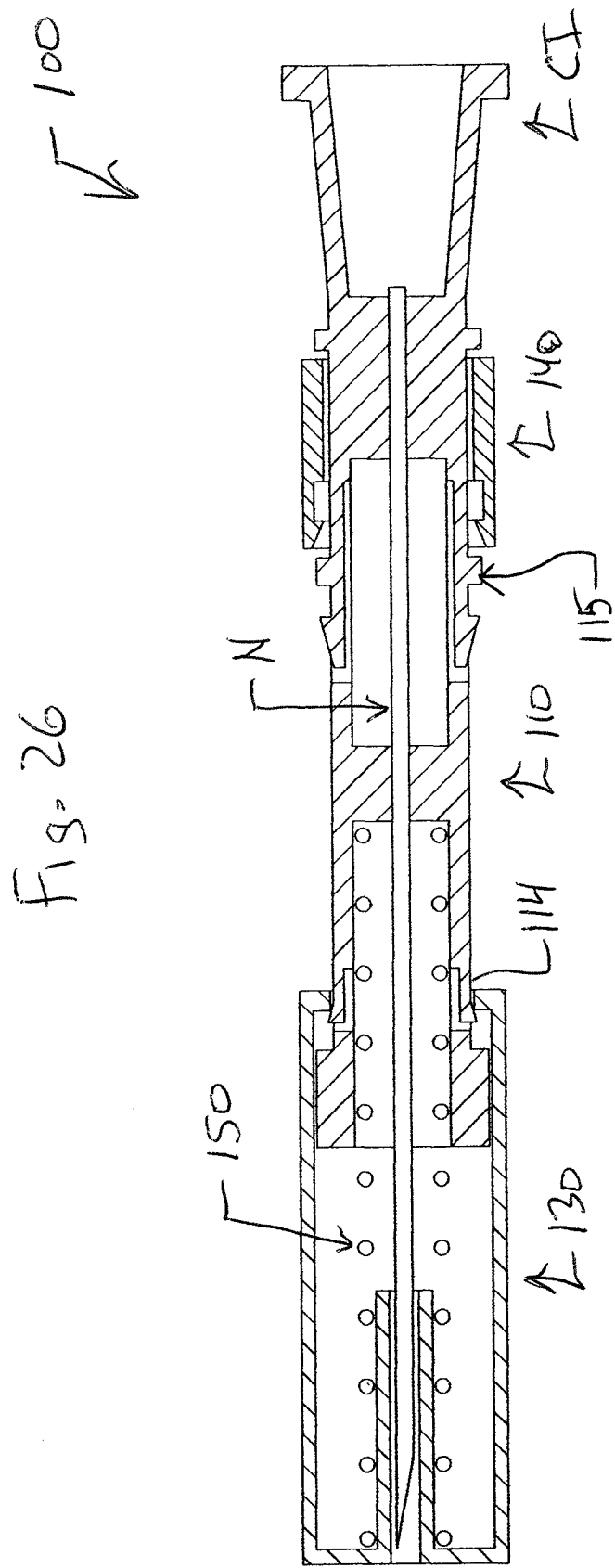
FIG. 26 shows a side cross-section view of another non-limiting embodiment of the device. The deflectable releasable locking member arranged behind the needle is not shown for clarity. This embodiment is similar to the device of FIGS. 1-13 except that a rear or distal end of the device utilizes a connecting interface or configuration allowing the device to be connected to a sample and/or injection device.

Referring now to FIG. 26 which shows another embodiment of an injection device 100. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device 100 includes an elongate generally cylindrical body or barrel 110 having a needle N retained therein. The needle N is hollow and has a proximal end that is configured for puncturing and a distal end for discharging or receiving fluid. The device 100 also utilizes an axially movable and retractable safety sleeve 130 arranged at a proximal end of the body 110 and an axially movable trigger sleeve 140 arranged at an area of a distal end of the body 110. Finally, the device 100 utilizes a spring 150 which is configured to bias the axially movable and retractable safety sleeve 130 towards an extended position covering the puncturing end of the needle N. The deflectable member 114 and 115 arranged behind the needle N are not shown for clarity. This embodiment is similar to the device of FIGS. 1-13 except that it additionally includes a connecting interface CI for connecting the device 100 to an injection device. In embodiments, the interface IC is a luer-lok or luer lock type interface.

Figure 27:
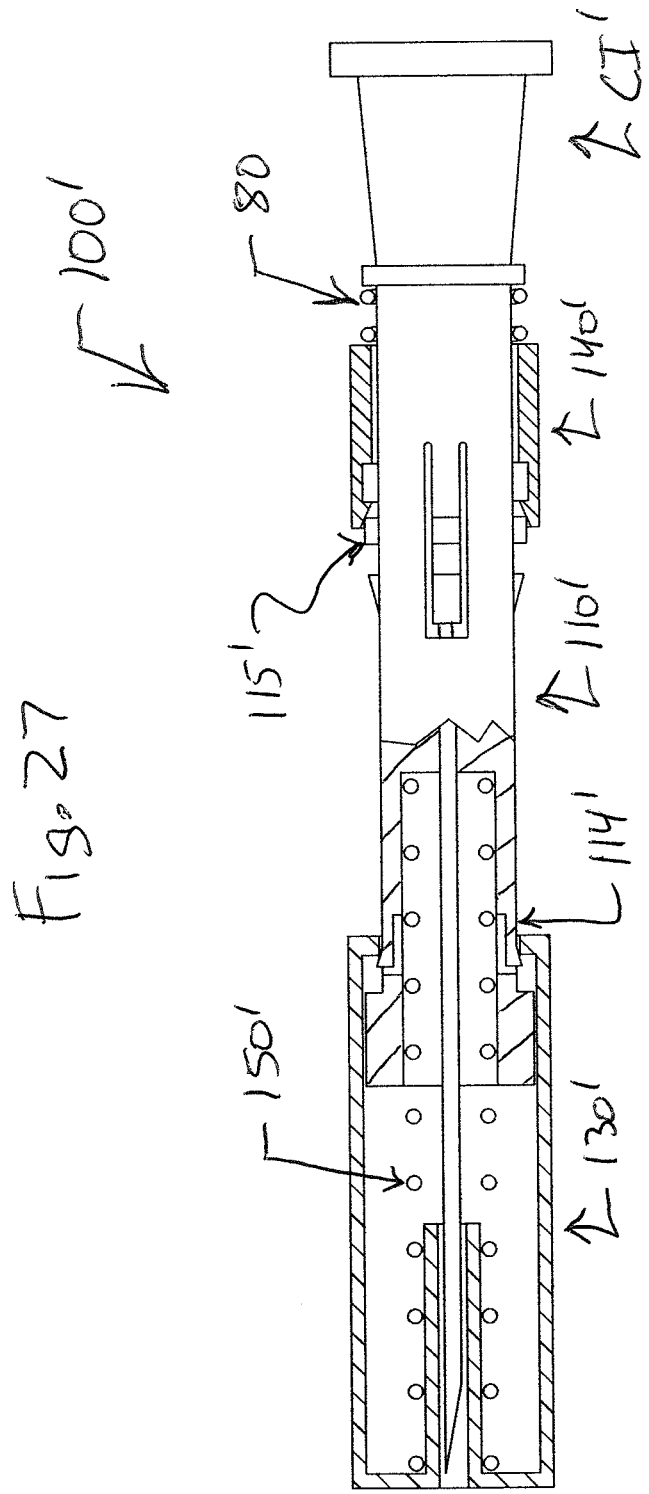
FIG. 27 shows a partial side cross-section view of another non-limiting embodiment of the device. This embodiment is similar to the device of FIG. 26 except that a trigger spring is utilized.

Referring now to FIG. 27 which shows another embodiment of an injection device 100'. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device 100' includes an elongate generally cylindrical body or barrel 110' having a needle N retained therein. The needle N is hollow and has a proximal end that is configured for puncturing and a distal end for discharging or receiving fluid. The device 100' also utilizes an axially movable and retractable safety sleeve 130' arranged at a proximal end of the body 110' and an axially movable trigger sleeve 140' arranged at an area of a distal end of the body 110'. Finally, the device 100' utilizes a spring 150' which is configured to bias the axially movable and retractable safety sleeve 130' towards an extended position covering the puncturing end of the needle N. The deflectable member 114' and 115' arranged behind the needle N are not shown for clarity. This embodiment is similar to the device of FIG. 27 except that it additionally includes a spring 80 for biasing the trigger sleeve 140' towards a forward position. In embodiments, the interface IC' is a luer-lok or luer lock type interface.

Figure 28:
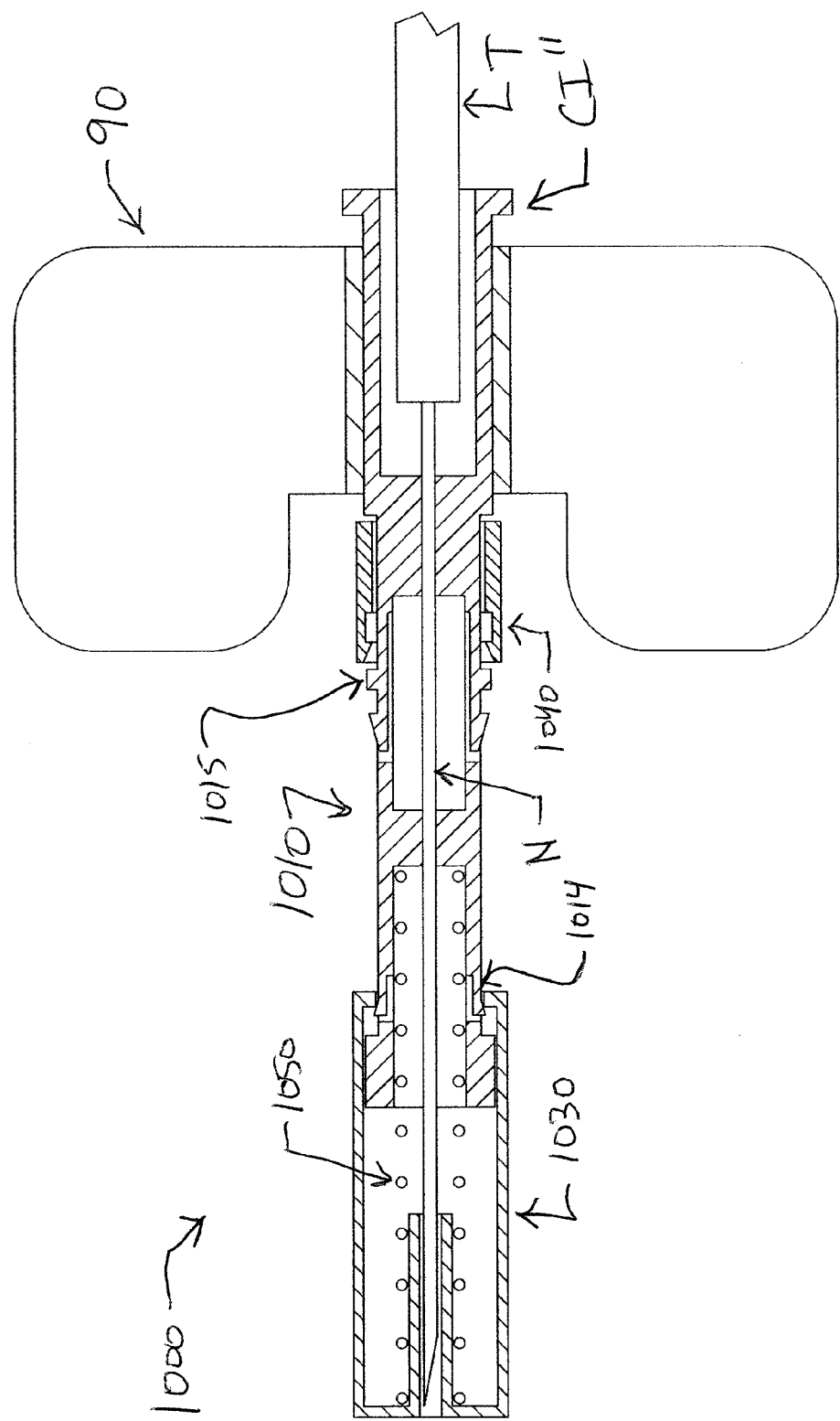

Referring now to FIGS. 28-30, which shows another embodiment of an injection device 1000. In embodiments, the device is a device for injecting an IV needle. In embodiments, the device is an injection device that can be coupled to a device for injection or obtaining a fluid sample. In embodiments, the device is used in combination with other devices in the context of healthcare delivery and/or the medical profession. As with the previous embodiment, the device 1000 includes an elongate generally cylindrical body or barrel 1010 having a needle N retained therein. The needle N is hollow and has a proximal end that is configured for puncturing and a distal end for discharging or receiving fluid. The device 1000 also utilizes an axially movable and retractable safety sleeve 1030 arranged at a proximal end of the body 1010 and an axially movable trigger sleeve 1040 arranged at an area of a distal end of the body 1010. Additionally, the device 1000 utilizes a spring 1050 which is configured to bias the axially movable and retractable safety sleeve 1030 towards an extended position covering the puncturing end of the needle N. The deflectable member 1014 and 1015 arranged behind the needle N are not shown for clarity. This embodiment is similar to the device of FIGS. 1-13 except that it additionally includes a connecting interface CI" for connecting the device 1000 to a fluid injection and/or removing device. In embodiments, the interface IC" includes an arrangement allowing a tube or tubing T to connect the device 1000 to the fluid container (not shown). The device 1000 also utilizes an axially retained removable butterfly member 90 arranged at a distal end of the body 1010. A non-limiting embodiment of the butterfly member is shown in FIG. 30. In embodiments, other butterfly members, whether conventional or otherwise, can be utilized with the devices disclosed herein such as that shown in FIG. 28.

The devices described herein can also utilize one or more features disclosed in prior art documents expressly incorporated by reference in pending U.S. patent application Ser. No. 11/616,196 (Publication No. 2008/0154212). This application/publication and the documents expressly incorporated therein is hereby expressly incorporated by reference in the instant application. Furthermore, one or more of the various parts of the device(s) can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any one or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A needle device configured so as to be attachable to a skin surface and capable of introducing an IV fluid when attached to the skin surface, the needle device comprising:
   a body comprising a front end and a rear end;
   the rear end of the body being structured and arranged to be connectable to an injection device, a fluid sample obtaining device, or a tube;
   a needle shield movable relative to the body at least between an initial position and a retracted position;
   a needle at least partially arranged in the body and having an axial length that is longer than an axial length of the needle shield; and
   a biasing member surrounding a portion of the needle and that causes the needle shield to move to an extended position when the needle device is activated by a user,
   wherein the needle device further comprises a safety system that includes an arrangement that at least one of:
      non-releasably locks the needle shield in an extended position and releasably retains the needle shield in the retracted position after the user moves the needle shield to the retracted position;
      prevents a user from triggering the device before use and non-releasably locks the needle shield in an extended position after use;
      non-releasably locks the needle shield in a fully extended position and is spaced from a trigger that when activated allows the needle shield to move under the action of the biasing member to an extended position;

can be activated to prevent the needle shield from being retained in a retracted position after a user moves the needle shield towards the retracted position;

non-releasably retains the needle shield in a fully extended position after being activated by a user and after being automatically moved to the fully extended position by the biasing member; and utilizes two separate and axially spaced apart re-use prevent mechanisms.

2. The device of claim 1, wherein the device is a single-use needle device.

3. The device of claim 1, wherein the body is generally cylindrically shaped.

4. The device of claim 1, wherein the needle shield is generally cylindrically shaped.

5. The device of claim 1, wherein the body comprises a one-piece member.

6. The device of claim 1, wherein the needle shield comprises a one-piece member.

7. The device of claim 1, wherein the body and the needle shield each comprise a synthetic resin material.

8. The device of claim 1, wherein the needle comprises a generally cylindrical hollow needle.

9. The device of claim 8, wherein the needle comprises at least one of metal and stainless steel.

10. The device of claim 1, wherein the body comprises at least one releasable retaining member which releasably retains the needle shield in the retracted position.

11. The device of claim 1, wherein the body comprises plural releasable retaining members which releasably retains the needle shield in the retracted position.

12. The device of claim 1, wherein the body comprises at least one non-releasable retaining member which non-releasably retains the needle shield in a fully extended position.

13. The device of claim 1, wherein the body comprises at least one non-deflectable retaining member which non-releasably retains the needle shield in an extended position.

14. The device of claim 1, wherein the body comprises plural non-releasable retaining members which lock the needle shield in an extended position.

15. The device of claim 1, wherein the needle shield is movable from the initial position that is intermediate the fully extended position and the retracted position to the retracted position and then to the fully extended position.

16. The device of claim 1, wherein the needle shield is movable to the retracted position from the initial position that is intermediate the fully extended position and the retracted position.

17. The device of claim 1, further comprising a trigger that selectively releases at least one locking member which releasably retains the needle shield in the retracted position.

18. The device of claim 1, wherein the biasing member is structured and arranged to automatically move the needle shield from the retracted position to the fully extended position.

19. The device of claim 1, wherein the biasing member is a helical compression spring structured and arranged to move the needle shield from the retracted position to the fully extended position.

20. The device of claim 1, wherein the biasing member is a helical compression spring structured and arranged to maintain the needle shield in an initial position.

21. The device of claim 1, wherein the safety system automatically causes the needle shield to move to the extended position when activated by a user.

22. The device of claim 1, wherein the safety system releasably retains the needle shield in the retracted position after the user moves the needle shield to the retracted position.

23. The device of claim 1, wherein the safety system prevents a user from triggering the device.

24. The device of claim 1, further comprising a connecting interface arranged at the rear end for allowing the device to be mounted to the injection device or the fluid sample obtaining device.

25. The device of claim 24, wherein the connecting interface has a luer lock type configuration.

26. The device of claim 1, further comprising a system preventing the user from inadvertently moving the needle shield to the retracted position from the initial position.

27. The device of claim 26, wherein the system preventing the user from inadvertently moving the needle shield to the retracted position from the initial position one of:
    requires the user to rotate and unthread the needle shield from the body; and
    requires the user to remove a removable use prevention device.

28. A single-use needle device configured so as to be attachable to a skin surface and capable of introducing an IV fluid when attached to the skin surface, the needle device comprising:
    a body comprising a front end and a rear end;
    the rear end of the body being structured and arranged to be connectable to an injection device, a fluid sample obtaining device, or a tube;
    a needle shield axially movable relative to the body at least between an initial position and a retracted position;
    a needle at least partially arranged in the body and having an axial length that is longer than an axial length of the body;
    a biasing member surrounding a portion of the needle and that causes the needle shield to move to an extended position when activated by a user; and
    an arrangement that at least two of:
        before the needle shield is non-releasably locked in an extended position, releasably retains the needle shield in the retracted position after the user moves the needle shield to the retracted position;
        prevents a user from triggering the device before use and non-releasably locks the needle shield in an extended position after use;
        non-releasably locks the needle shield in a fully extended position and is spaced from a trigger that when activated allows the needle shield to move under the action of the biasing member to an extended position; and
        utilizes two separate axially spaced re-use prevent mechanisms.

29. An IV infusion needle device comprising:
    a body;
    a needle shield movable relative to the body at least between an initial position and a retracted position;
    a needle at least partially arranged in the body and having an axial length longer than either the needle shield or the body; and
    a safety system comprising a biasing member surrounding a portion of the needle and that causes the needle shield to move to an extended position when activated by a user, wherein said safety system further includes an arrangement that at least one of:
- releasably retains the needle shield in the retracted position after the user moves the needle shield to the retracted position;
- prevents a user from triggering the device;
- locks the needle shield in a fully extended position;
- prevents the needle shield from being retained in a retracted position after a user moves the needle shield towards the retracted position;
- non-releasably retains the needle shield in a fully extended position after being activated by a user; and
- utilizes two separate re-use prevent mechanisms.

30. A method of using the device of claim 1, the method comprising:
- moving the needle shield from an initial position to the retracted position;
- causing the needle shield to move to a fully extended position whereby the needle shield projects out beyond a needle tip;
- at least one of:
  - preventing the needle shield from moving back to the initial position; and
  - preventing the needle shield from being retained in the retracted position.

31. The device of claim 29, wherein the needle at least one of:
- has an axial length that is longer than an axial length of the needle shield; and
- has a distal end which extends back axially in the body farther than a distal end of the needle shield when the needle shield is arranged in an initial position.

32. The device of claim 1, wherein the needle at least one of:
- has an axial length that is longer than an axial length of the needle shield; and
- has a distal end which extends back axially in the body farther than a distal end of the needle shield when the needle shield is arranged in an initial position.

33. The device of claim 1, wherein an axial length of the needle is greater than an axial length of the body and the body contains therein the biasing member.

34. The device of claim 28, wherein the needle at least one of:
- has an axial length that is longer than an axial length of the needle shield; and
- has a distal end which extends back axially in the body farther than a distal end of the needle shield when the needle shield is arranged in an initial position.

35. A single-use IV needle device structured and arranged to be connectable to an injection device, a fluid sample obtaining device, or a tube, the needle device comprising:
- a body;
- a connecting interface connectable to an injection device, a fluid sample obtaining device, or a tube;
- an axially movable needle shield;
- a needle having a portion fixed within the body and a puncturing portion;
- a biasing member surrounding a portion of the needle and being structured and arranged to move the needle shield to an extended position; and
- a system that each of:
  - non-releasably locks the needle shield in a fully extended position; and
  - releasably retains the needle shield in the retracted position after the user moves the needle shield to the retracted position from an initial position.

* * * * *